(12) United States Patent
Lure et al.

(10) Patent No.: US 11,651,862 B2
(45) Date of Patent: May 16, 2023

(54) SYSTEM AND METHOD FOR DIAGNOSTICS AND PROGNOSTICS OF MILD COGNITIVE IMPAIRMENT USING DEEP LEARNING

(71) Applicant: MS Technologies, Rockville, MD (US)

(72) Inventors: Yuan-Ming Fleming Lure, Potomac, MD (US); Jing Li, Marietta, GA (US); Teresa Wu, Gilbert, AZ (US); David Weidman, Phoenix, AZ (US); Kewei Chen, Chandler, AZ (US); Xiaonan Liu, Seattle, WA (US); Yi Su, Phoenix, AZ (US)

(73) Assignee: MS TECHNOLOGIES, Rockville, MD (US)

( * ) Notice: Subject to any disclaimer, the term of this patent is extended or adjusted under 35 U.S.C. 154(b) by 0 days.

(21) Appl. No.: 17/866,021

(22) Filed: Jul. 15, 2022

(65) Prior Publication Data

US 2022/0367056 A1    Nov. 17, 2022

Related U.S. Application Data

(63) Continuation-in-part of application No. 17/857,963, filed on Jul. 5, 2022, and a continuation-in-part of
(Continued)

(51) Int. Cl.
| | | |
|---|---|---|
| *G16H 50/20* | (2018.01) | |
| *G16H 50/70* | (2018.01) | |
| *G16H 30/40* | (2018.01) | |
| *A61B 5/00* | (2006.01) | |
| *G16H 30/20* | (2018.01) | |

(52) U.S. Cl.
CPC ........... *G16H 50/20* (2018.01); *A61B 5/4088* (2013.01); *G16H 30/20* (2018.01); *G16H 30/40* (2018.01); *G16H 50/70* (2018.01)

(58) Field of Classification Search
CPC ........ G16H 50/20; G16H 30/20; G16H 30/40; G16H 50/70; A61B 5/4088
See application file for complete search history.

(56) References Cited

U.S. PATENT DOCUMENTS

| | | |
|---|---|---|
| 7,428,323 B2 | 9/2008 | Hillman |
| 9,367,817 B2 | 6/2016 | Schaffer et al. |
| (Continued) | | |

*Primary Examiner* — Ojiako K Nwugo
(74) *Attorney, Agent, or Firm* — Galvin Patent Law LLC; Brian R. Galvin

(57) ABSTRACT

A system and method for predicting mild cognitive impairment (MCI) related diagnosis and prognosis utilizing deep learning. More specifically, the system and method produce predictions of MCI conversions to Alzheimer's/dementia and prognosis related thereof. Using available medical imaging and non-imaging data a diagnosis and prognosis model is a deep learned model trained using transfer learning. An MCI-DAP server may then receive a request from a clinician to process predictions related to a target patient's diagnosis or prognosis. The target patient's medical data is retrieved and used to create a model for the target patient. Then details of the target patient's model and the diagnosis and prognosis model are compared, a prediction is generated, and the prediction is returned to the clinician. As new medical data becomes available it is fed into the respective model to improve accuracy and update predictions.

18 Claims, 18 Drawing Sheets

Related U.S. Application Data application No. 17/559,680, filed on Dec. 22, 2021, which is a continuation-in-part of application No. 17/116,686, filed on Dec. 9, 2020, now Pat. No. 11,380,181.

(60) Provisional application No. 63/150,335, filed on Feb. 17, 2021.

(56) References Cited

U.S. PATENT DOCUMENTS

| | | | | |
|---|---|---|---|---|
| 2014/0304200 | A1* | 10/2014 | Wall | G16H 10/20 |
| | | | | 706/12 |
| 2018/0310870 | A1* | 11/2018 | Givon | G06T 7/0014 |
| 2019/0183403 | A1* | 6/2019 | Gand | A61B 5/7267 |
| 2019/0272922 | A1* | 9/2019 | Albright | G06N 3/0445 |
| 2020/0013165 | A1 | 1/2020 | Zhang et al. | |
| 2020/0126221 | A1* | 4/2020 | El-Baz | G16H 30/20 |
| 2020/0260977 | A1* | 8/2020 | Kang | A61B 5/7275 |
| 2021/0138249 | A1* | 5/2021 | Howard | A61N 1/36082 |
| 2021/0158523 | A1* | 5/2021 | Khademi | G06T 5/40 |
| 2022/0073986 | A1* | 3/2022 | Nalls | G16H 50/20 |
| 2022/0180964 | A1* | 6/2022 | Sullivan | G06T 7/13 |
| 2022/0230731 | A1* | 7/2022 | Gilutz | G06N 3/0445 |

* cited by examiner

SYSTEM AND METHOD FOR DIAGNOSTICS AND PROGNOSTICS OF MILD COGNITIVE IMPAIRMENT USING DEEP LEARNING

CROSS-REFERENCE TO RELATED APPLICATIONS

Priority is claimed in the application data sheet to the following patents or patent applications, the entire written description of each of which is expressly incorporated herein by reference in its entirety:
Ser. No. 17/559,680
63/150,335
Ser. No. 17/116,686

BACKGROUND

Field of the Art

The disclosure relates to the field of transfer learning, and more particularly to the field of image data fusion and deep learning for personalized medical diagnostics and prognostics.

Discussion of the State of the Art

More than 5 million people in the US currently have Alzheimer's Disease (AD), and the number is expected to increase to 16 million by 2050. The direct health care cost is over $200 billion per year and projected to reach $1.2 trillion by 2050. Recent clinical trials designed to treat AD at the mild-to-moderate dementia phase have been largely unsuccessful. There is a growing consensus that treatment should target the disease in its early phases before irreversible brain damage occurs. Mild Cognitive Impairment (MCI) is a prodromal phase of AD at which patients experience cognitive decline but have not developed dementia. Treatment at the MCI phase could potentially delay the progression to AD or even prevent the patient from developing AD. However, early detection of AD at the MCI phase has been a significant clinical challenge because of the heterogeneity of MCI patients. That is, the cognitive impairment of a patient may be caused by various underlying diseases not just AD. As a result, conventional cognitive assessment based on clinical criteria for diagnostics of MCI fall short in differentiating "MCI due to AD" from other possibilities.

To address this MCI diagnostic challenge, NIA and the Alzheimer's Association (AA) published a new criterion in 2011 to facilitate the detection of MCI due to AD. The Criteria include amyloid and neuronal injury biomarkers, in addition to cognitive assessment, to risk-stratify MCI into sub-groups of high, intermediate, and low likelihoods due to AD, an isolated amyloid pathology sub-group (IAP), and a suspected non-AD pathophysiology sub-group (SNAP). This represents a significant milestone in MCI diagnostics.

However, despite recent developments, the current clinical capability for MCI diagnostics is still limited. The existing clinical tools focus only on single imaging modalities. Although various machine learning methods have been developed for multi-modality structural and functional imaging data fusion and demonstrated better performance than using a single modality alone, the research so far has not been transferred into a clinically-feasible technology. The research so far does not offer integration capability across different modalities to leverage their joint strength. There are attempts at multi-modality solutions but are solely focusing on image co-registration and pre-processing, and not advanced machine learning (ML) to generate accurate and robust diagnostic and prognostic results. General ML algorithms for multi-modality integration fall short for providing real clinical utility. This is because their modeling strategies typically do not account for the reality that patients may not have all the image modalities available due to cost, insurance coverage, and other accessibility constraints. This limits the usage and commercialization potential of the existing ML algorithms.

What is needed is a system and method that can integrate multi-modality image data across many patients to produce individual diagnostic and prognostic predictions for patients with incomplete modalities.

What is needed is a system and method for diagnostics and prognostics of mild cognitive impairment that can use deep learning to integrate multi-modality image data across many patients and produce individual diagnostic and prognostic predictions for patients with incomplete modalities.

SUMMARY

Accordingly, the inventor has conceived and reduced to practice, a system and method for predicting mild cognitive impairment (MCI) related diagnosis and prognosis utilizing deep learning. More specifically, the system and method produce predictions of MCI conversions to Alzheimer's/dementia and prognosis related thereof. Using available medical imaging and non-imaging data a diagnosis and prognosis model is a deep learned model trained using transfer learning. An MCI-DAP server may then receive a request from a clinician to process predictions related to a target patient's diagnosis or prognosis. The target patient's medical data is retrieved and used to create a model for the target patient. Then details of the target patient's model and the diagnosis and prognosis model are compared, a prediction is generated, and the prediction is returned to the clinician. As new medical data becomes available it is fed into the respective model to improve accuracy and update predictions.

According to a first preferred embodiment, a system for diagnostics and prognostics of mild cognitive impairment is disclosed, comprising: a computer system comprising a memory and a processor; a deep learning engine, comprising a first plurality of programming instructions stored in the memory and operating on the processor, wherein the first plurality of programming instructions, when operating on the processor, causes the computer system to: retrieve a plurality of patient data; process the data into training data subsets; use the one or more training data subsets to train one or more predictive diagnosis- and prognosis-related deep learning models, wherein each of the one or more predictive diagnosis- and prognosis-related deep learning models are trained using a different training data subset; apply transfer learning to the one or more predictive diagnosis- and prognosis-related deep learning models to integrate available modalities, wherein the integrated modalities are used to train a deep learning classifier to output an accurate diagnostic or prognostic prediction; receive a diagnosis- or prognosis-related request for a target patient; retrieve a plurality of target patient data; input the target patient data into the deep learning classifier; and output the target patient's prediction.

According to a second preferred embodiment, a method for diagnostics and prognostics of mild cognitive impairment is disclosed, comprising the steps of: retrieving a plurality of patient data; processing the data into training data subsets; using the one or more training data subsets to train one or more predictive diagnosis- and prognosis-related deep learning models, wherein each of the one or more predictive diagnosis- and prognosis-related deep learning models are trained using a different training data subset; applying transfer learning to the one or more predictive diagnosis- and prognosis-related deep learning models to integrate available modalities, wherein the integrated modalities are used to train a deep learning classifier to output an accurate diagnostic or prognostic prediction; receiving a diagnosis- or prognosis-related request for a target patient; retrieving a plurality of target patient data; inputting the target patient data into the deep learning classifier; and outputting the target patient's prediction.

According to an aspect of an embodiment, the plurality of patient data comprises medical imaging data, medical non-imaging data, and a combination of both.

According to an aspect of an embodiment, the deep learning engine is further configured to: train a predictive model of a target patient; find one or more matches between the deep learning classifier and the predictive model of the target patient; use the one or more matches to identify diagnosis- or prognosis-related predictions of the target patient; and output the target patient's predictions.

According to an aspect of an embodiment, an image processing engine, comprising a second plurality of programming instructions stored in the memory and operating on the processor, wherein the second plurality of programming instructions, when operating on the processor, causes the computer system to: receive medical imaging data; preprocess the medical imaging data; and send the preprocessed medical imaging data to the deep learning engine.

According to an aspect of an embodiment, a data processing pipeline, comprising a third plurality of programming instructions stored in the memory and operating on the processor, wherein the third plurality of programming instructions, when operating on the processor, causes the computer system to: receive medical non-imaging data; preprocess the medical non-imaging data; and send the preprocessed medical non-imaging data to the deep learning engine.

According to an aspect of an embodiment, the one or more deep learning models is a reverse multi-task recurrent neural network and wherein the deep learning classifier is a reverse multi-task recurrent neural network.

According to an aspect of an embodiment, the target patient's predictive model is updated when new medical data becomes available.

According to an aspect of an embodiment, the updated target patient's predictive model outputs an updated diagnosis, prognosis, or both.

According to an aspect of an embodiment, the plurality of the target patient's medical data is incomplete.

According to an aspect of an embodiment, medical imaging data is selected from the group of MRI, FDG-PET, amyloid-PET, FLAIR, DTI, fMRI, Florbetapir-PET, and any combination thereof.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

Figure 12A:
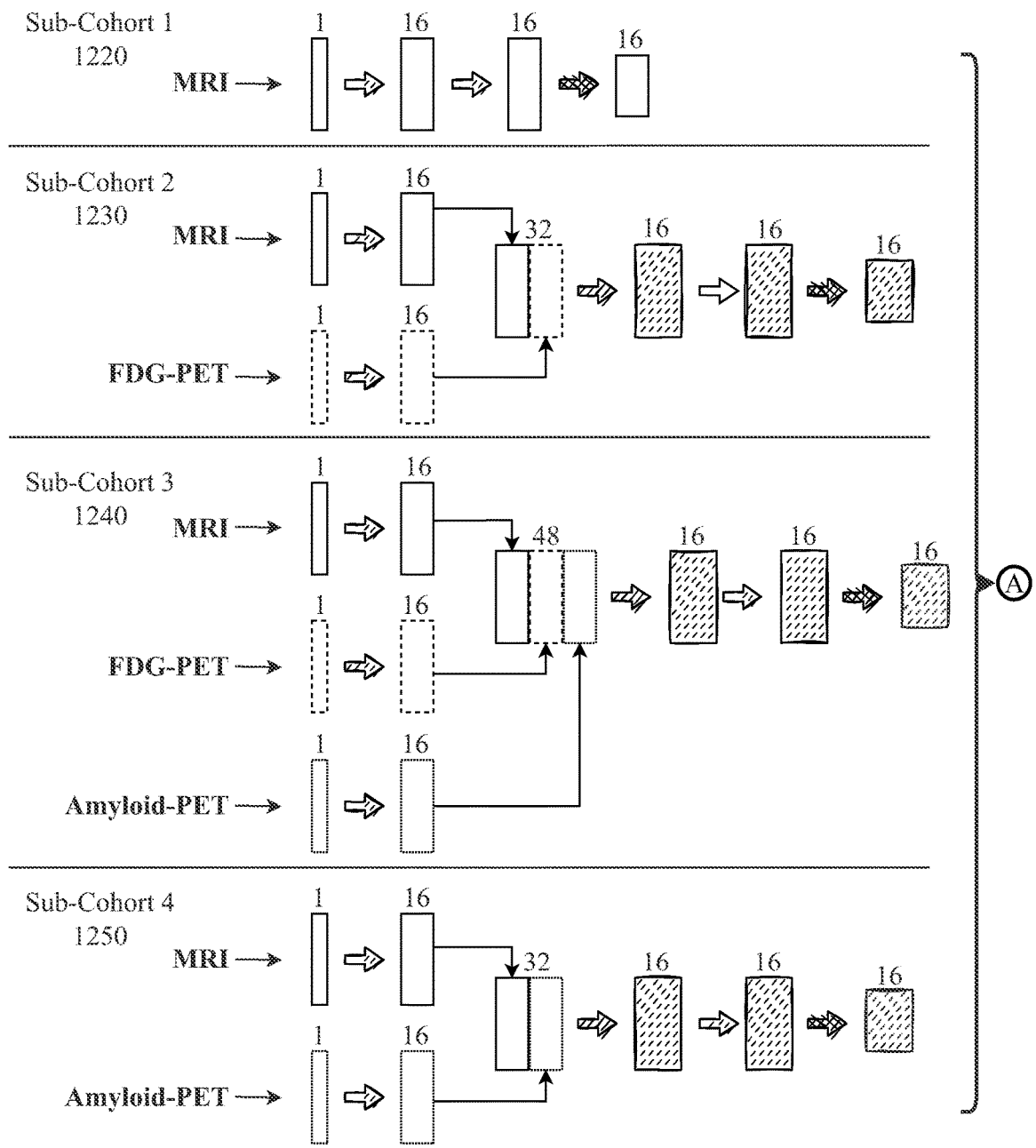
Figure 12B:
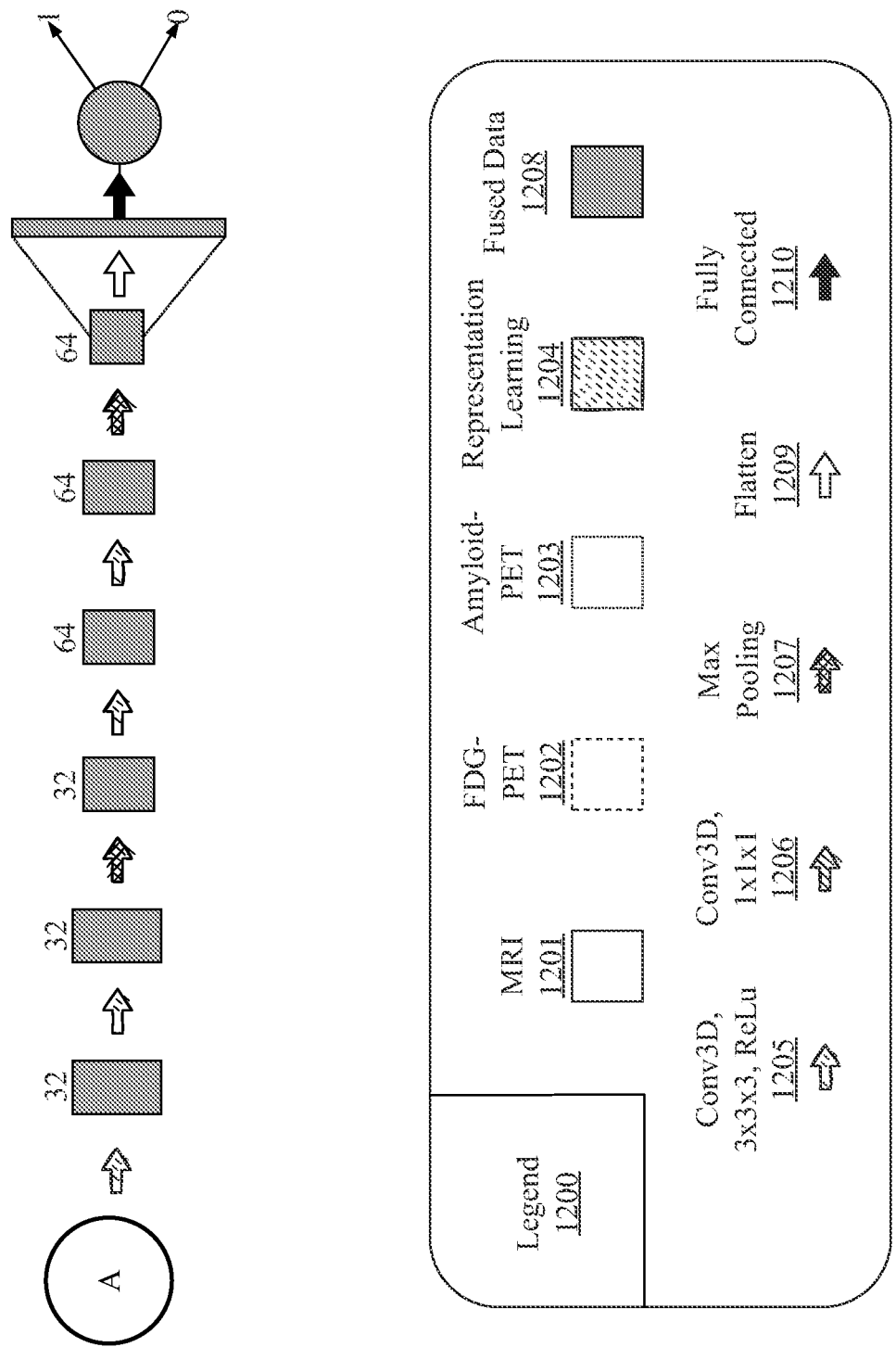

FIGS. 12A and 12B describe an exemplary configuration of an incomplete multi-modality transfer learning algorithm integrated with a deep learning algorithm (IMTL-DL), according to an aspect.

Figure 13:
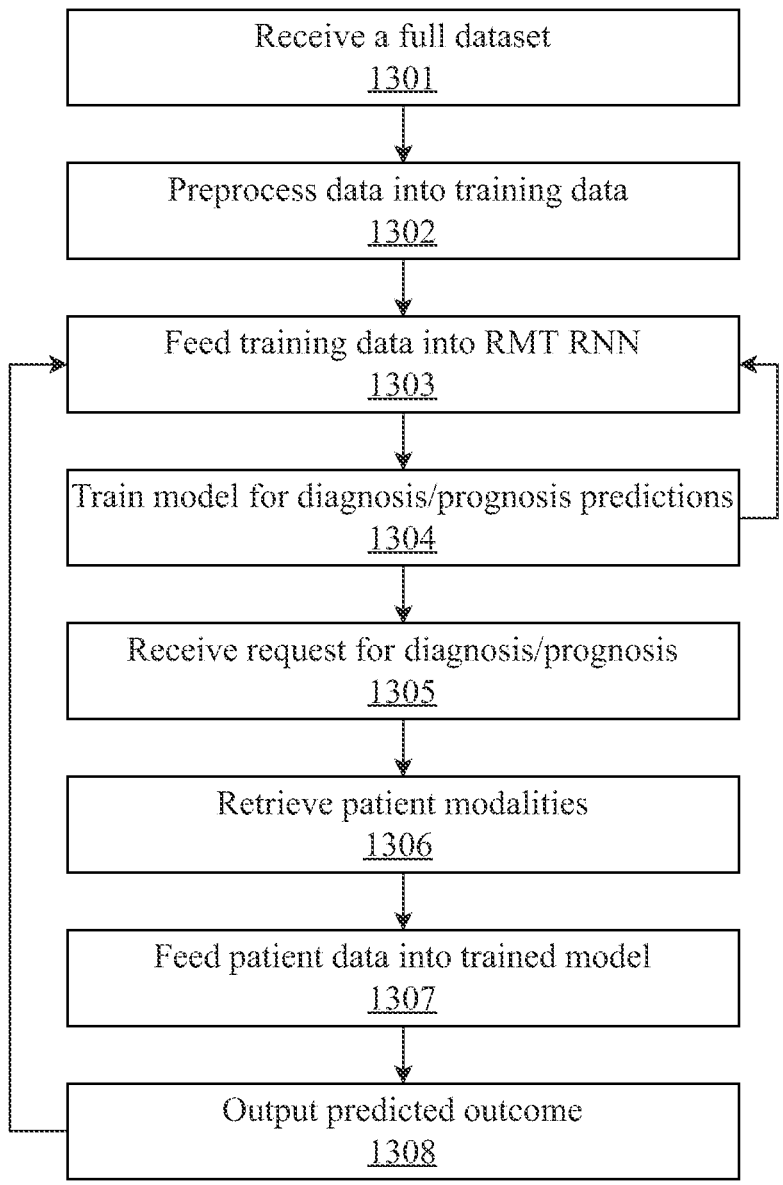

FIG. 13 is a method diagram illustrating an exemplary workflow to output predicted outcomes using the ITML-DL model.

Figure 14:
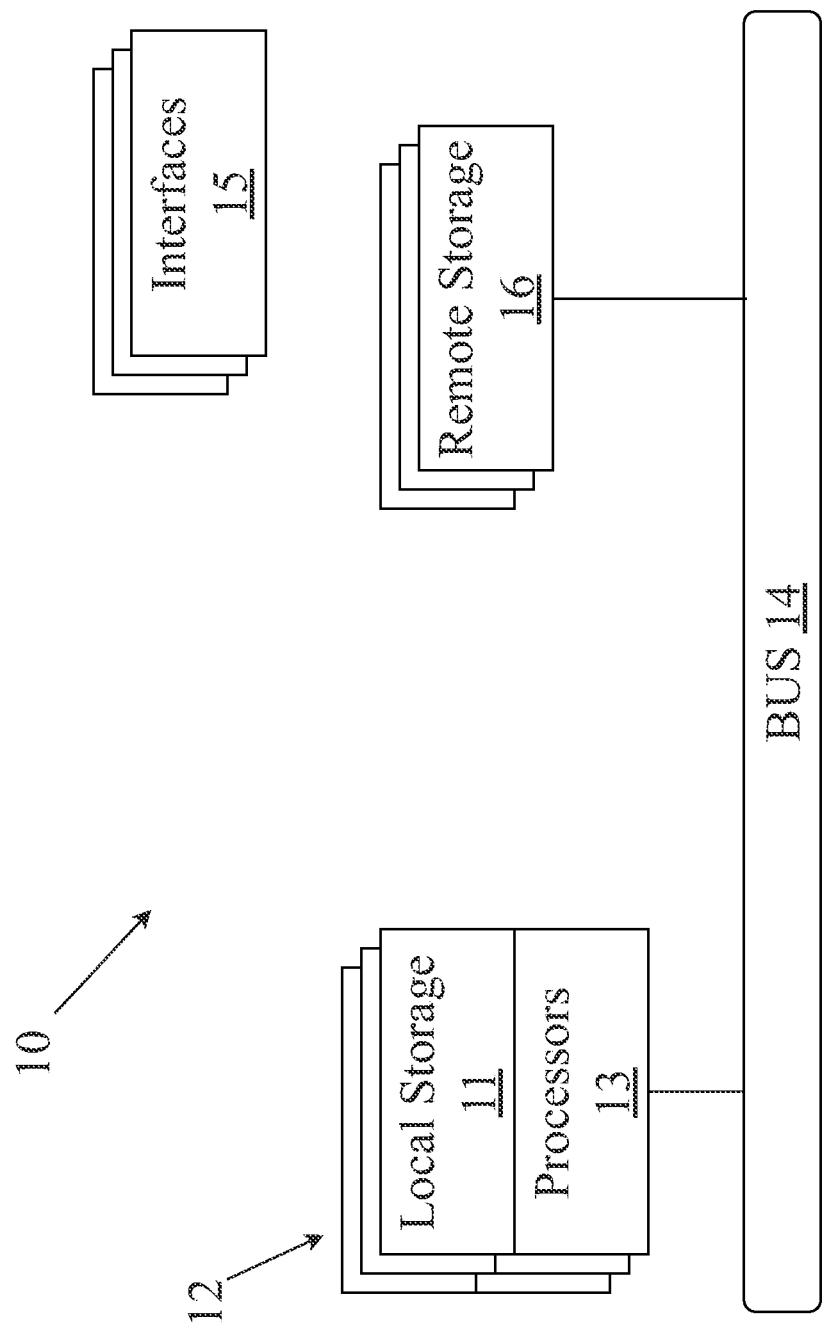

FIG. 14 is a block diagram illustrating an exemplary hardware architecture of a computing device.

Figure 15:
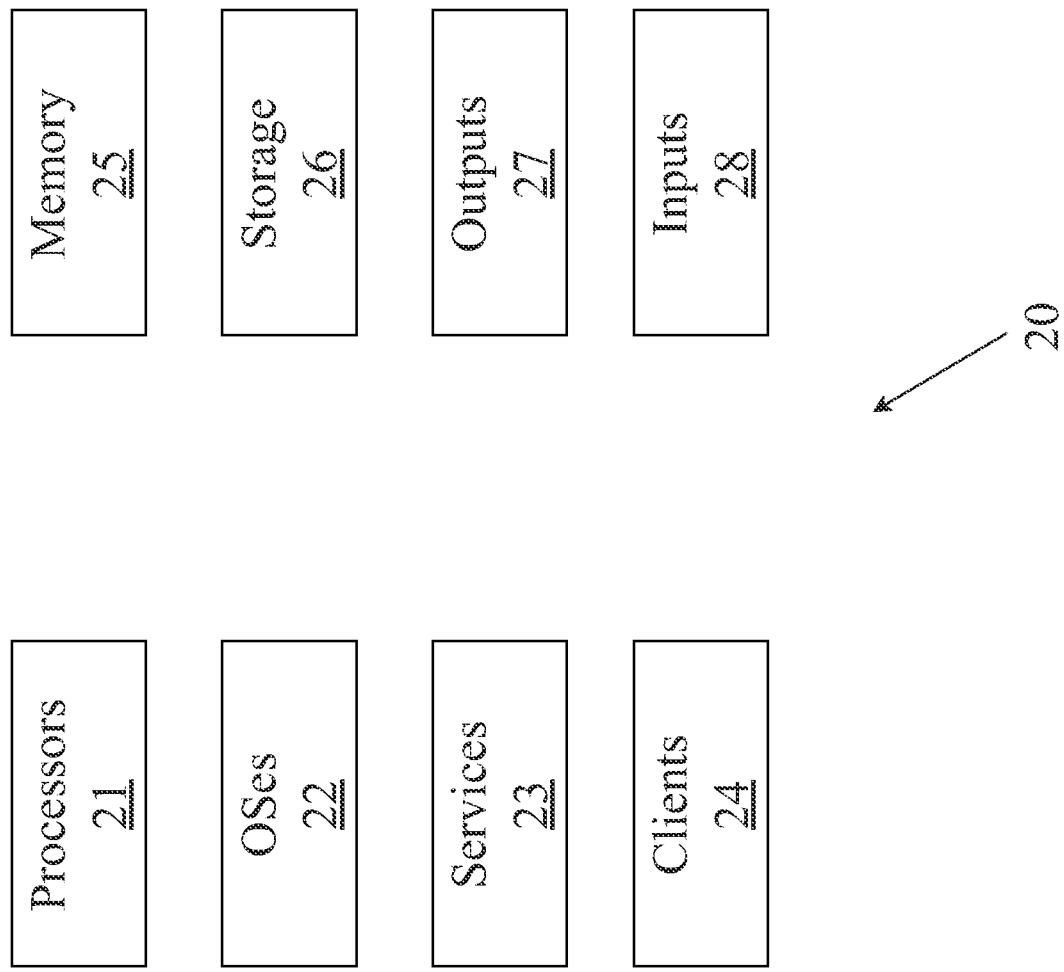

FIG. 15 is a block diagram illustrating an exemplary logical architecture for a client device.

Figure 16:
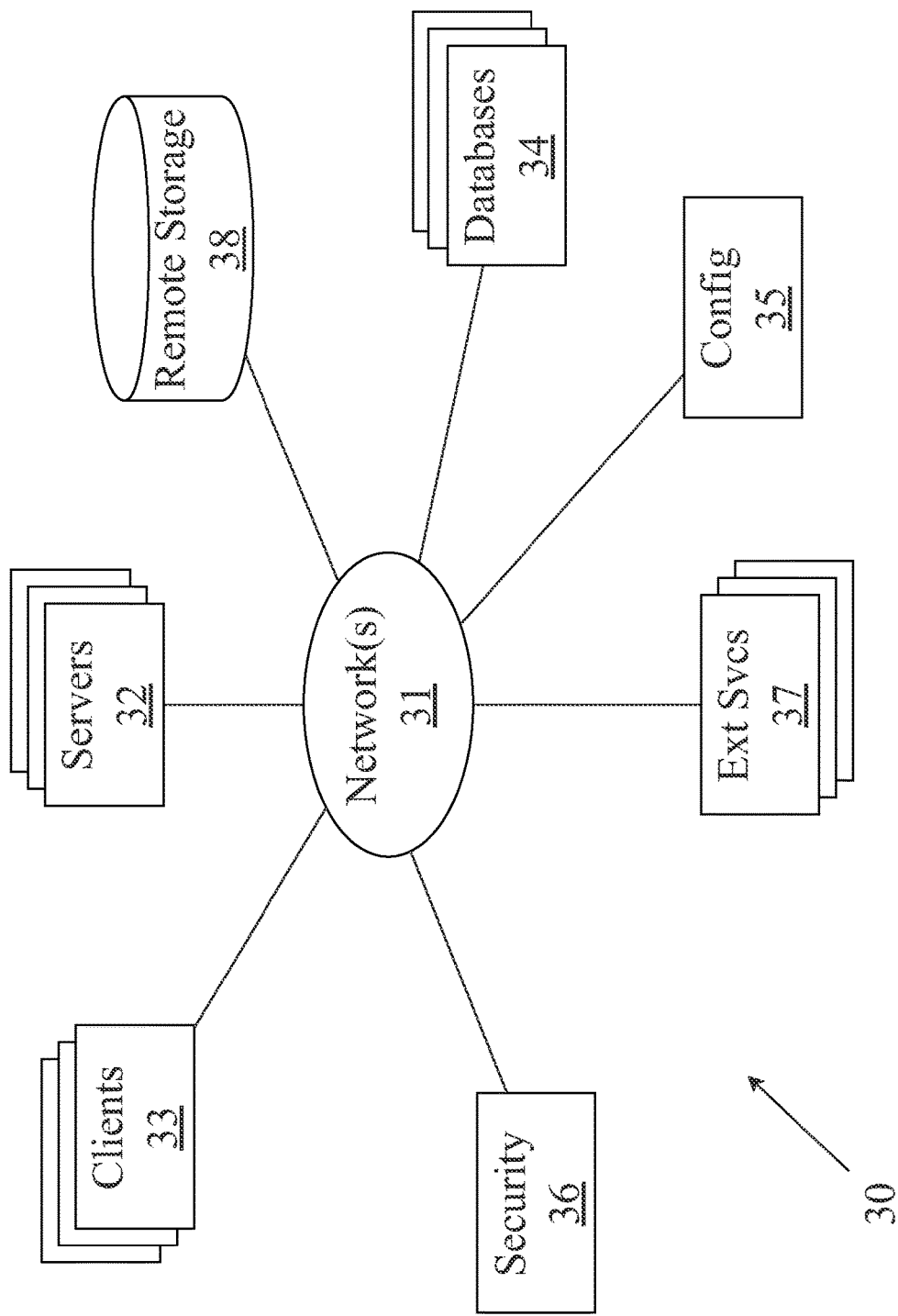

FIG. 16 is a block diagram showing an exemplary architectural arrangement of clients, servers, and external services.

Figure 17:
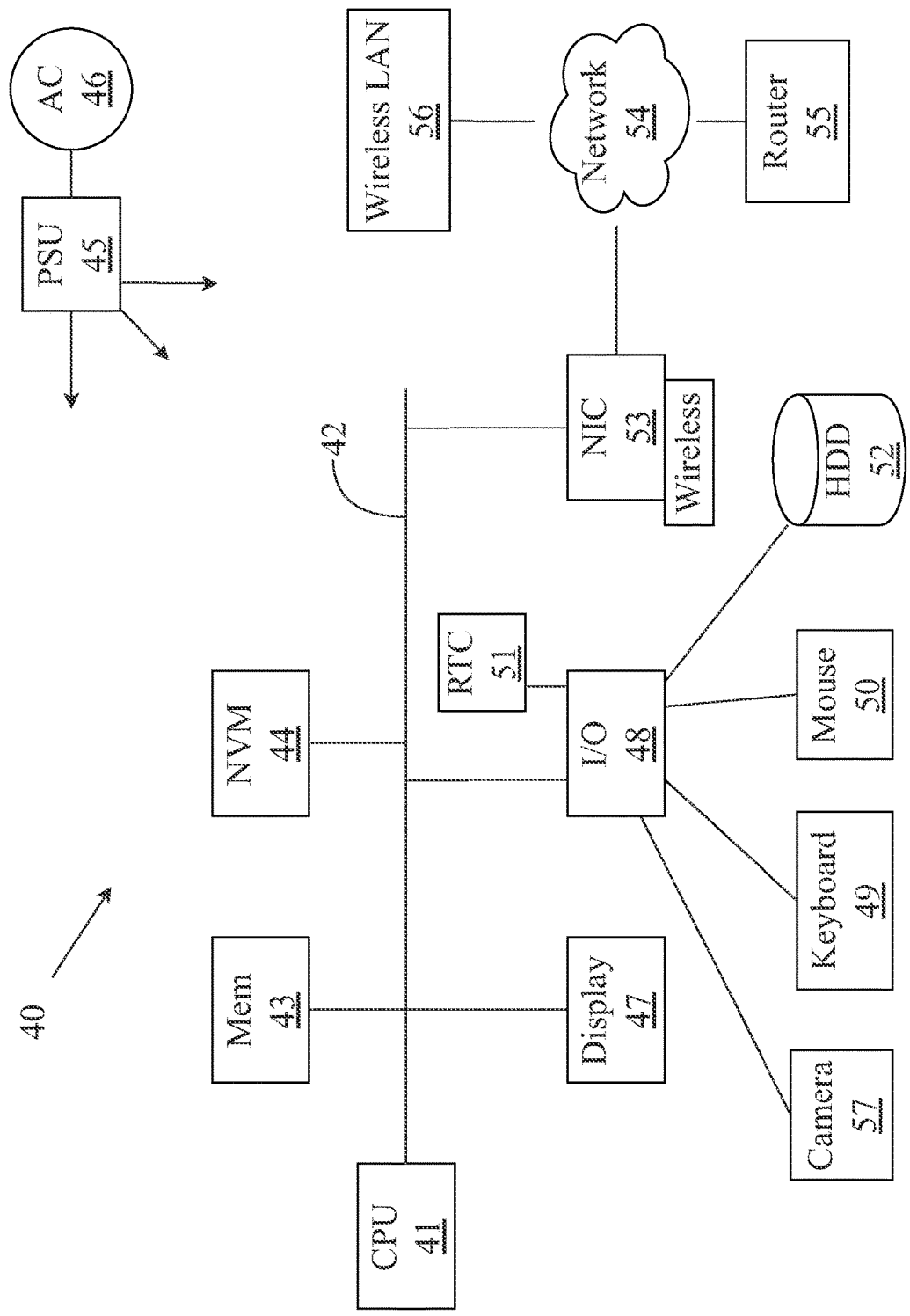

FIG. 17 is another block diagram illustrating an exemplary hardware architecture of a computing device.

DETAILED DESCRIPTION

The inventor has conceived, and reduced to practice, a system and method for predicting mild cognitive impairment (MCI) related diagnosis and prognosis utilizing deep learning. More specifically, the system and method produce predictions of MCI conversions to Alzheimer's/dementia and prognosis related thereof. Using available medical imaging and non-imaging data a diagnosis and prognosis model is a deep learned model trained using transfer learning. An MCI-DAP server may then receive a request from a clinician to process predictions related to a target patient's diagnosis or prognosis. The target patient's medical data is retrieved and used to create a model for the target patient. Then details of the target patient's model and the diagnosis and prognosis model are compared, a prediction is generated, and the prediction is returned to the clinician. As new medical data becomes available it is fed into the respective model to improve accuracy and update predictions.

Software for Computer Aided Detection of Early Stage Lung Cancer can be integrated directly into digital chest imaging products manufactured by major industry vendors. It can also be configured into industry standard hardware for sales into stand alone, traditional film-based, chest x-ray environments . . . And it can be integrated into PC server hardware to support the more than 34,000 networked digital chest imaging devices installed throughout the world today.

As disclosed herein, various embodiments rise above current state-of-the-art by using novel "multitask learning" and "transfer learning" methods for learning of MCI diagnostic and prognostic models from a dataset collected at a single time point, in which multi-modality images are not universally available across all the patients. Such a dataset is called a cross-sectionally partially-available multi-modality dataset (CPAMD). Multitask learning is a popular modern machine learning area that simultaneously model multiple related domains called "tasks" by allowing effective knowledge and data sharing. According to various embodiments, each task is defined to be a patient cohort in the dataset who has the same available imaging modalities at the focused time point (e.g., baseline). Multitask learning will produce a diagnostic/prognostic model specific to each patient cohort (i.e., task), but the model estimation process uses the data of all the patients jointly rather than cohort-by-cohort. Such a joint estimation exploits the fact that different patient cohorts may share some modalities though not all. This makes the tasks not completely independent and therefore warrants multitask learning. A significant advantage of multitask learning is that the joint estimation has a virtual effect of increasing the sample size of each task. This is important for producing a model for each patient cohort with high power, considering that the samples size of each cohort may be small.

Furthermore, within each patient cohort, multi-modality images that are available at baseline may not be universally available at each follow-up visit, and this temporal availability pattern of multi-modality images may also be patient-specific. This results in a so-called longitudinally partially-available multi-modality dataset (LPAMD) for each patient cohort. According to various embodiments, transfer learning is used to model each LPAMD. Transfer learning is also a popular modern machine learning area that integrates the model of an old domain and the data of a new domain in order to model the new domain with better accuracy. The old-domain model is defined to be the diagnostic/prognostic model obtained at an earlier time point (e.g., baseline), and the new-domain data to be multi-modality images available at a follow-up visit (e.g., six months). Transfer learning will produce an updated diagnostic/prognostic model at the follow-up visit, using not only the new image data but also the old model by assuming that the updated model coefficients have a smooth change with respect to the old model coefficients, and the change is proportional to the time interval between the two visits. This assumption is grounded in the fact that MCI is a continuously evolving process. Transfer learning can naturally model LPAMD, because it transfers the old-domain model instead of the data, and therefore does not require the same imaging modalities to be available for the two domains (i.e., two time points).

One anticipated embodiment comprises another function of the machine learning algorithms which is to generate the missing modality images. Using training data and a generative adversarial network (or other machine learning algorithm) the missing modalities of patients may be generated such that the generated images further inform the predictive accuracy of a multi-modality transfer learning algorithm (IMTL).

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"CLPAMD" or "cross-sectionally and longitudinally partially-available multi-modality dataset" as used herein means a dataset comprising multi-modality images from a specific point in time and longitudinal data of temporal availability/unavailability patterns on the same imaging modalities before or after short-term follow-up visits, both of which may not universally available across all the patients in the dataset.

"MCI" or "mild cognitive impairment" as used herein means a neurocognitive disorder which involves cognitive impairments beyond those expected based on an individual's age and education, but which are not significant enough to interfere with instrumental activities of daily living. MCI may occur as a transitional stage between normal aging and dementia, especially Alzheimer's disease.

Conceptual Architecture

Figure 1:
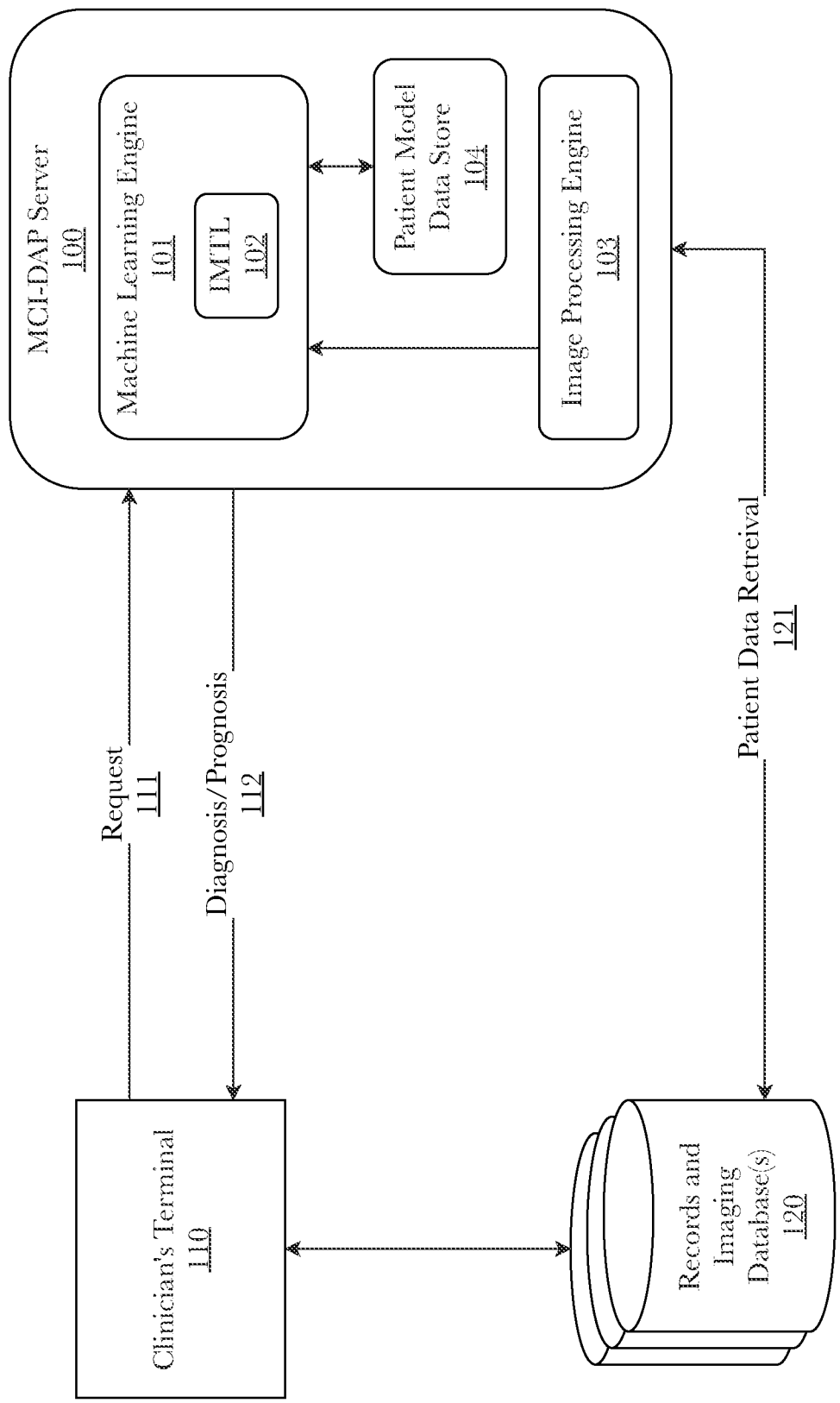
FIG. 1 is a block diagram illustrating an exemplary system architecture for a mild cognitive impairment—diagnostic and prognostic (MCI-DAP) server.

FIG. 1 is a block diagram illustrating an exemplary system architecture for a mild cognitive impairment—diagnostic and prognostic (MCI-DAP) server 100. According to various embodiments, a mild cognitive impairment—diagnostic and prognostic (MCI-DAP) server 100 comprises a machine learning engine 101 utilizing an incomplete multi-modality transfer learning algorithm (IMTL) 102, a patient model data store 104 which stores learned models and associated data, and an image processing engine 103 which prepares images for machine learning applications. The server may be communicatively coupled to a clinician's terminal 110 and a records and imaging database(s) 120, whereby a clinician may request 111 to receive predictions 112 from the MCI-DAP server 100 which retrieves patient data 121 from one or more records and imaging databases 120 and outputs a prediction 112. The records and imaging database 120 is also typically networked with radiology and other hospital departments such that a patient's image data is co-located with other medical information. Furthermore, the records and imaging database 120 as disclosed herein is merely exemplary and represents any digital or analog data store that holds image data and other medical data pertaining to patients.

The machine learning engine 101 employing the incomplete multi-modality transfer learning algorithm (IMTL) 102 does not require filling in the modality-wise missing data. With an end goal to train an ML model for each patient sub-cohort, IMTL 102 couples the processes of training the sub-cohort-wise models together using an iterative EM algorithm to allow information transfer between the models. This is different from SM of each sub-cohort, with benefit of augmenting the sample size of each sub-cohort using the transferred information served as virtual samples, and thus producing estimators for the model coefficients with less variance—a nice statistical property leading to less variability (thus robustness) of using the model to make a diagnosis/prognosis. Mathematical details are disclosed in FIG. 4.

The IMTL model 102 may be developed using incomplete multi-modality imaging data collected at a single time point (i.e., at the baseline visit). Consider the exemplary dataset in FIG. 2 to illustrate an exemplary model of development, however, IMTL 102 is generalizable to other types of modality-wise missing data. Consider one diagnostic model for each sub-cohort in FIG. 2, i.e., $f_1(X_{MRI}, Z)$, $f_2(X_{MRI}, X_{FDG}, Z)$, $f_3(X_{MRI}, X_{FDG}, X_{Amyloid}, Z)$ $f_4(X_{MRI}, X_{Amyloid}, Z)$, respectively. $X_{MRI}$, $X_{FDG}$, and $X_{Amyloid}$ contain features extracted from the corresponding imaging modality. Z contains non-imaging covariates such as gender, age, and education level. $f_i(\bullet)$, i=1, . . . , 4, is a classifier that takes features of the available image modalities and the covariates as input, and outputs a probability for MCI due to AD for each subject. This probability can be further converted to a binary output of MCI due to vs. not due to AD using a cutoff if needed.

If conventional ML were used, the classifiers would be trained separately using each sub-cohort's specific data, which would suffer from small sample size. In IMTL 102, the training processes of sub-cohort-wise models are coupled together. In detail, these models are put into a unified form, $f(X,Z)=\text{logistic}(\beta_0+\beta_x^T X+\beta_z^T Z)$. X contains features from all imaging modalities. Parts of X are not available for sub-cohorts 1, 2, and 4, and therefore treated as latent variables. The conditional distribution of the latent variables given the observed imaging features as $X_{latent} \sim N(\gamma_0+\gamma_1^T X_{observed}, \Sigma)$. Let $\Theta$ contain all the parameters to be estimated, i.e., $\Theta=\{\beta_0, \beta_x, \beta_z, \gamma_0, \gamma_1, \Sigma\}$. To estimate $\Theta$, the commonly used Maximum Likelihood Estimation (MLE) approach does not work because of the latent variables. According to one aspect, an Expectation-Maximization (EM) algorithm (see also FIG. 4) is used to alternate between deriving the expectation of the latent variables (called the E step) and estimating the model parameters in $\Theta$ (called the M step) until convergence. Once done, we can further derive the classifier for each sub-cohort, i.e., $$f_1(X_{MRI}, Z)=\text{logistic}(\beta_{10}+\beta_{1,MRI}^T X_{MRI}+\beta_{1,z}^T Z) \text{ sub for sub-cohort 1;}$$

$$f_2(X_{MRI}, X_{FDG}, Z)=\text{logistic}(\beta_{02}+\beta_{2,MRI}^T X_{MRI}+\beta_{2,FDG}^T X_{FDG}+\beta_{2,z}^T Z) \text{ for sub-cohort 2;}$$

$$f_3(X_{MRI}, X_{FDG}, X_{Amyloid}, Z) = \text{logistic}\left(\begin{array}{c}\beta_{03} + \beta_{3,MRI}^T X_{MRI} + \beta_{3,FDG}^T X_{FDG} \\ + \beta_{3,Amyloid}^T X_{Amyloid} + \beta_{3,z}^T Z\end{array}\right)$$

for sub-cohort 3;

$$f_4(X_{MRI}, X_{Amyloid}, Z) = \text{logistic}\left(\begin{array}{c}\beta_{04} + \beta_{4,MRI}^T X_{MRI} + \beta_{4,Amyloid}^T X_{Amyloid} \\ + \beta_{z,4}^T Z\end{array}\right)$$

for sub-cohort 4;
where the $\beta$'s are functions of the estimated parameters $\hat{\Theta}$ from the EM algorithm. Note that the form of the above models looks like that the models are separately trained for each sub-cohort, but they are not. By introducing latent variables and using the EM algorithm, the model coefficients of each sub-cohort are estimated based on all the available training data instead of just the data specific for that sub-cohort. In this way, knowledge obtained from the modeling of each sub-cohort can be "transferred" to assist the modeling of other sub-cohorts. For example, the knowledge gained for modeling sub-cohort 3 that consists of all imaging modalities, in terms of correlation between the three modalities and their respective predictability to the diagnostic result, can be transferred to the models of the other sub-cohorts with missing modalities such as sub-cohort 1 with only MRI, sub-cohort 2 with only MRI & FDG-PET, etc.

Similar transference happens between other sub-cohorts. This knowledge transfer helps achieve high accuracy of diagnosis for sub-cohorts even with missing modalities. Another example is that the estimators for model parameters by IMTL, i.e., $\hat{\Theta}$, have a larger Fisher information (equivalent to a smaller variance) than the estimators produced by separate modeling. This translates into smaller variability in using the trained IMTL to make a diagnosis. This theoretical property of IMTL ensures its good performance beyond empirical observations. Prognostic model building by IMRT follows the similar procedure except that classifiers need to be trained to classify converters vs non-converters by a pre-defined future time T.

When imaging data is available at multiple time points (e.g., both baseline and a follow-up visit), incorporating the changes in imaging features in IMTL 102 improves the diagnostic/prognostic accuracy. Let $\delta X$ denote the rates of changes in the imaging features. Using rates helped normalize the different time intervals between the follow up and baseline across different patients. $\delta X$ may be added to the original feature set that contained only the baseline imaging features to re-train the diagnostic and prognostic models. Note that $\delta X$ included latent variables corresponding to the missing modalities. Therefore, a similar EM algorithm to the one developed for cross-sectional IMTL was used to estimate the parameters of the models.

Figure 2:
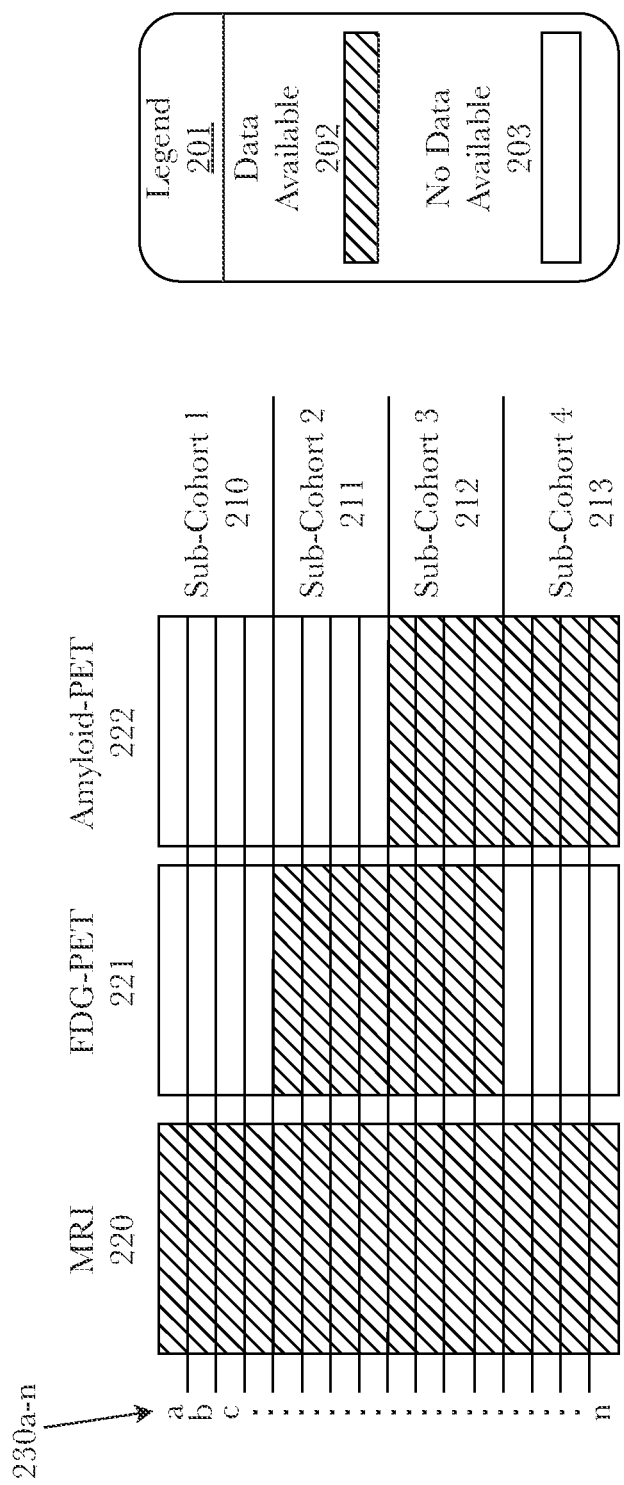
FIG. 2 is a block diagram illustrating an exemplary table of incomplete multi-modality data.

FIG. 2 is a block diagram illustrating an exemplary table of incomplete multi-modality data. This diagram is an example of an incomplete multi-modality image dataset that can be modeled by IMTL. MRI 220, FDG-PET 221, and amyloid-PET 222 are considered as three modalities, however, other modalities may be considered such as FLAIR, DTI, fMRI, and Florbetapir-PET. Columns within each modality represent image features—refer to the legend 201 for data availability 202 or non-availability 203 of modalities according to the table. Patients in sub-cohort 3 212 have all imaging modalities available, whereas the other sub-cohorts 210, 211, 213 only have partially available (a.k.a. incomplete) imaging modalities. Not all patients have all image modalities available due to cost, equipment availability, insurance coverage, and other accessibility constraints. The novelty of IMTL, compared with existing ML algorithms, is to use Transfer Learning (TL) to integrate available image modalities of each patient 230a-n to produce an accurate result. This capability warrants the broad utility to patients and clinics with varying resources and imaging accessibility.

Figure 3:
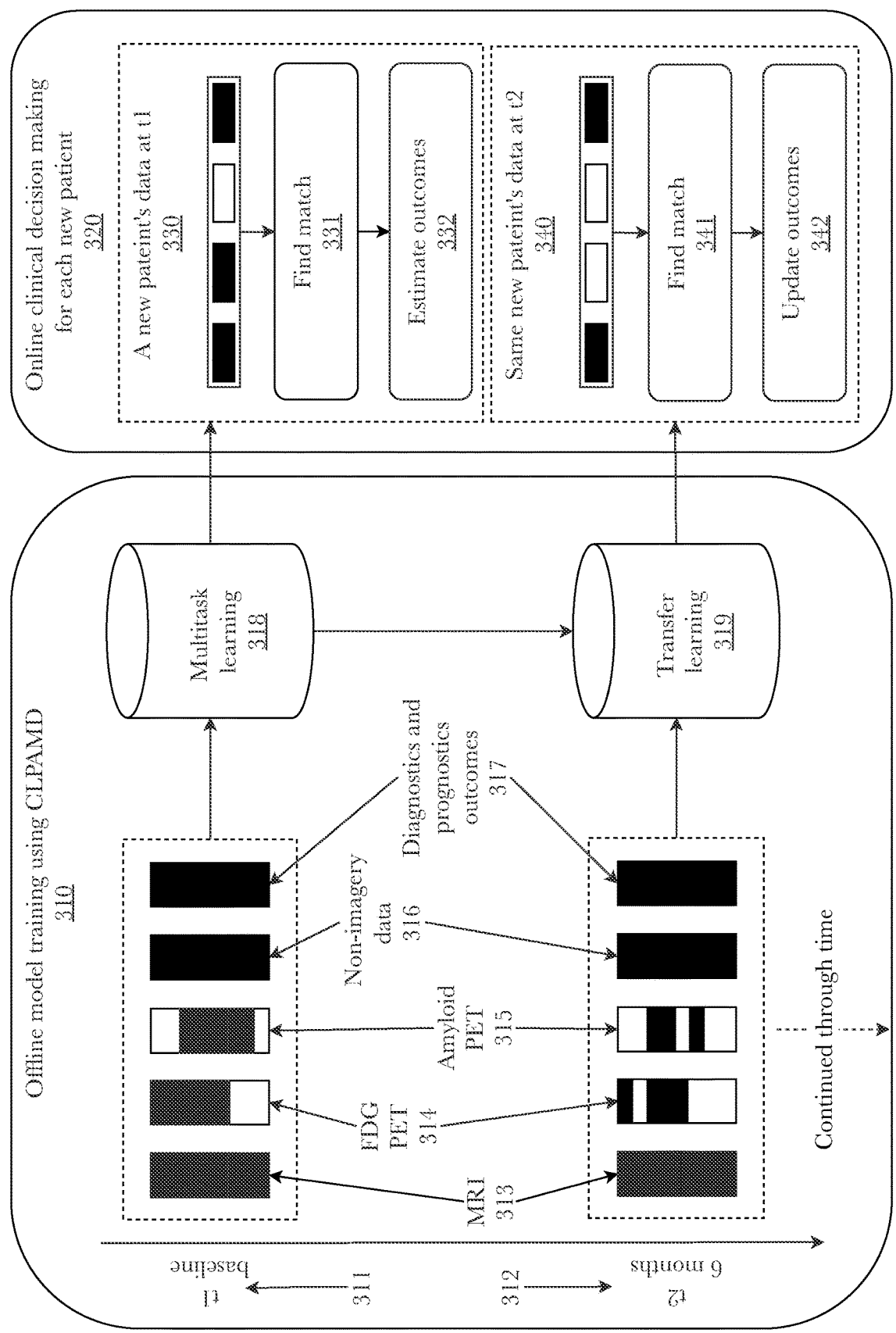
FIG. 3 is a block diagram illustrating an exemplary system architecture for diagnostic and prognostic predictions using a cross-sectionally partially-available multi-modality dataset.

FIG. 3 is a block diagram illustrating an exemplary system architecture for diagnostic and prognostic predictions using a cross-sectionally partially-available multi-modality dataset. This diagram illustrates an exemplary overall system architecture of the MCI-DAP Server (multi-modality imaging availability—black is available and white is unavailable—as shown in the CLPAMD 313-317 is for illustration purposes and may not reflect real data).

The MCI-DAP Server comprises an "offline model training using CLPAMD" module 310 and an "online clinical decision making" module 320. According to one embodiment, the offline module 310 is run at the backend. It takes in a CPAMD 313-317 of n existing patients, collected at time t1 (e.g., baseline) 311, and applies multitask learning 318 to produce a diagnostic/prognostic model for each patient cohort that has the same available imaging modalities. Next, the offline module 310 combines the t1 model for each patient cohort and the LPAMD for the same cohort collected at t2 (e.g., six months) 312 by transfer learning 319, and produces updated diagnostic/prognostic models for each cohort at t2. This process is repeated until diagnostic/prognostic models for every time point of interest are obtained.

The "online clinical decision making" module 320 is the frontend that a clinician interacts with. Specifically, when seeing a new patient for the first time (i.e., baseline), the clinician will feed the patient's available imaging modalities 330 into the online module 320. The online module 320 will first find a patient cohort in training that matches with the new patient's available imaging modalities 331. Then, it will use the corresponding training model of that cohort to produce a diagnostic and prognostic result for the new patient 332. At a follow-up visit (e.g., six months) for the same patient, the clinician will feed the patient's newly collected data from the follow-up visit into the online module 340. The online module 320 will first find a matching cohort in training at the same follow up time interval 341, and then use the corresponding training model to produce an updated diagnostic and prognostic result for the patient 342.

One exemplary method of modeling of CPAMD 313-317 using multitask learning 318 in order to produce powerful and accurate diagnostic and prognostic models is disclosed. Diagnostic and prognostic models at a single time point (e.g., baseline) from a CPAMD of n existing patients are developed. "A suite of models" is developed to generate complementary results for clinicians to cross-reference and better inform their decisions. These models are different in their outcome measures, but they will use the same CPAMD. For diagnostic modeling, consider the outcome variable to be binary, i.e., MCI due to AD or not due to AD. For prognostic modeling, consider two types of outcome variables: (1) A binary outcome of conversion vs. non-conversion to AD within a certain timeframe. Multiple time points can be considered such as baseline, six months, one year, etc. (2) A survival type of outcome, i.e., the time to conversion or censoring time.

Figure 7:
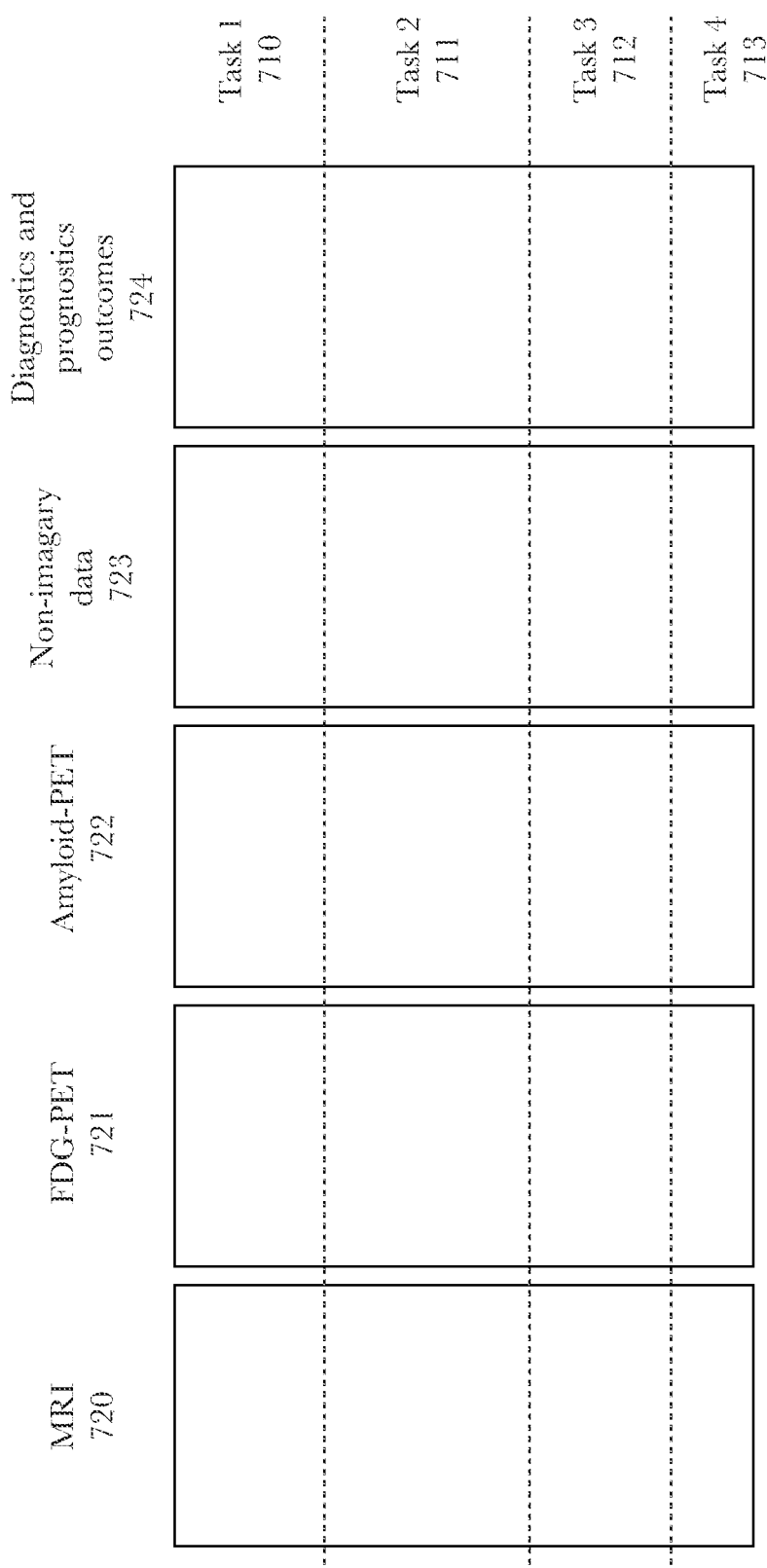
FIG. 7 is a block diagram illustrating an exemplary cross-sectionally partially-available multi-modality dataset and the definition of tasks.

To develop a multitask learning model, each task is defined to be a patient cohort in the CPAMD, who has the same available imaging modalities. FIG. 7 shows an example of an exemplary definition of tasks. Then, a Bayesian approach is employed to account for task correlation by assuming the model coefficients of all the tasks share a common prior distribution. Combining this prior and the available data of each patient cohort (i.e., task) through a Maximum-A-Posterior (MAP) estimation will produce a model for each task. In this way, the tasks are modeled together, which allows for the modeling processes of the tasks to borrow strength from each other. Also, to handle data high-dimensionality, a sparsity-induced penalty is added to the MAP formulation to produce a sparse model. Sparse learning is a modern machine learning area that provides one of the most effective solutions to the modeling of "small n large p" datasets. This proposed multitask learning method 318 can flexibly model various types of outcome variables; then according to one aspect, "plug" the likelihood function specific to each aforementioned outcome into the same modeling framework.

Regarding deliverables for clinical use, multitask learning 318 is used in the offline module 310 to model the CPAMD and produce a diagnostic model and a set of prognostic models with various types of outcome measures for each patient cohort. For a new patient coming to a clinic, his/her available imaging modalities will be used to identify a matching cohort, and the corresponding training models of that cohort will be used to generate diagnostic and prognostic results for that patient. The results will include an estimated probability of MCI due to AD, and probabilities of conversion to AD by a number of future time points as well as an estimated time to conversion. These various results could then be cross-referenced and used to help the clinician make a better-informed decision.

Modeling of LPAMD using transfer learning 319 in order to produce updated diagnostic and prognostic models with improved accuracy. For each patient cohort, the diagnostic and prognostic models should be continuously updated upon the availability of new data at follow-up visits. Not all the imaging modalities available at one time point (e.g., baseline) are repeated measured at every other data point (e.g., some follow-ups). This results in a LPAMD for each patient cohort. To fit an updated model at a follow-up, one intuitive approach is to use only the new data of the available imaging modalities at that follow-up. A Bayesian transfer learning method is one exemplary method to account for the disease evolution by assuming the old model coefficients obtained at the previous time point as a prior mean for the updated model coefficients at the follow-up visit. The prior covariance is a function of the time difference between the two visits. In essence, this prior distribution assumes that the updated model coefficients have a "smooth change" with respect to the old model coefficients, and the change is proportional to the time interval of the two visits (the closer the follow-up visit to the previous one, the smaller the change). Combining this prior and the new data of the available imaging modalities through an MAP estimation will produce an updated model at the follow-up visit. For a similar consideration to multitask learning, a sparsity-induced penalty is added to the MAP formulation to handle data high-dimensionality. Note that because the proposed transfer learning method transfers the old model but not the old data, it does not require same available imaging modalities for the two visits, and therefore can naturally model LPAMD.

Regarding data preprocessing, MRI processing and feature extraction uses a computational pipeline to perform cortical reconstruction and volumetric segmentations for structural MRI and extract 305 features including average and standard deviation of cortical thickness, the volumes of cortical parcellations, the volumes of specific white matter parcellations, and the total surface area of the cortex. This pipeline is used to batch-process longitudinal MRI images. Regarding F18 amyloid PET and FDG-PET processing and feature extraction according to one embodiment extracts features using various brain atlas and voxel-based approaches. Other non-imaging data may include the longitudinal data of cognitive tests, demographics (age and education) and APOE status. Additional data pipelines may be used to preprocess non-imaging data such as age, gender, and other patient-specific data.

Outcome data for diagnostic modeling, may be a binary outcome variable, Y=1 if the subject has a high likelihood due to AD and Y=0 if not. The NIA-AA Criteria may be used for this classification. For prognostic modeling, two types of outcome variables are anticipated: (1) A binary outcome of conversion vs. non-conversion to AD by a certain time point. Multiple time points will be considered such as six months, one year, 18 months, and two years. (2) A survival type of outcome, i.e., the time to conversion or censoring time.

The entire data is split into a training set and test set according to one aspect. Then multitask and transfer learning is used to train diagnostic and prognostic models, and apply these models to the test set to compute accuracy. This may be done for different splits of the data and also use cross validation, and compute the average accuracy. For diagnostic/prognostic models with a binary outcome, one approach disclosed may be to compute the sensitivity, specificity, and Area Under the Curve (AUC) that is robust to tuning parameter and threshold selections. To evaluate the accuracy of the prognostic model with a survival type of outcome, a cox models approach is disclosed to compare the predicted and observed survival functions.

A notable benefit of the proposed multitask and transfer learning methods is that they will naturally allow for "feature selection" because of the sparse learning formulation. That is, they will identify a small subset of features from the high-dimensional imaging and non-imaging data that are most significantly associated with a diagnostic or prognostic outcome. These features can be considered as diagnostic/prognostic markers, which have enormous value for drug trials.

Through the disclosed embodiments, the results will be an innovative and cost-effective approach to significantly enhance and extend the existing diagnostic Criteria for personalized diagnostics and prognostics system for MCI due to AD. Further, various embodiments will provide much accurate diagnostic and prognostic tool by integrating multi-modality measurements and allowing the system to learn new cases in real-time or near-real time fashion.

Figure 4:
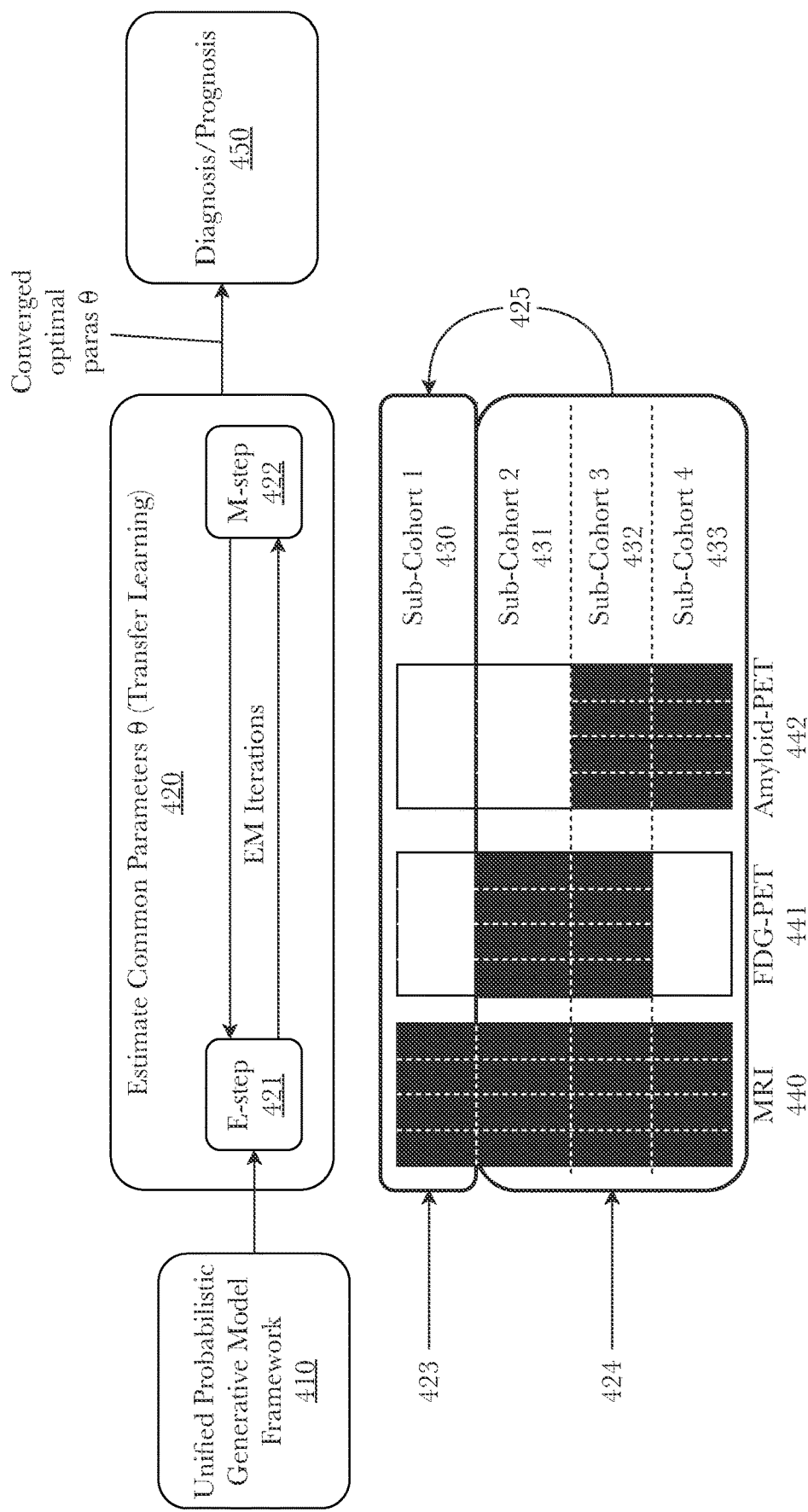
FIG. 4 is a block diagram illustrating an exemplary learning architecture for an incomplete multi-modality transfer learning model.

FIG. 4 is a block diagram illustrating an exemplary learning architecture for an incomplete multi-modality transfer learning model. According to one embodiment, knowledge is transferred 425 from different sub-cohorts 423, 424 and different modalities 440, 441, 442 to make better prediction on each sub-cohort 430-433, where the sub-cohorts model framework is a unified probabilistic generative model 410. According to one aspect of various embodiments, the unified probabilistic generative model framework 410 comprises a likelihood function (x: available modality; x̃: missing modality) and within the framework each sub-cohort may be mathematically expressed as described below:

$l_1(\theta) = p_\theta(y, x^{MRI}, \tilde{x}^{FDG}, \tilde{x}^{AYD}|z)$  Sub-cohort 1:

$l_2(\theta) = p_\theta(y, x^{MRI}, x^{FDG}, \tilde{x}^{AYD}|z)$  Sub-cohort 2:

$l_3(\theta) = p_\theta(y, x^{MRI}, x^{FDG}, x^{AYD}|z)$  Sub-cohort 3:

$l_4(\theta) = p_\theta(y, x^{MRI}, \tilde{x}^{FDG}, x^{AYD}|z)$  Sub-cohort 4:

Knowledge transferred is accomplished by first estimating the classification models for each of sub-cohorts 430-433. Then calculating the common parameters 420 which is the knowledge, and transfer the knowledge among sub-cohorts using E-M-based algorithms 421, 422. Diagnostic/prognostic model 450 for the patient within each sub-cohort is derived using Bayes' rule and marginalization:

$(y|x^{MRI}, z)$  Sub-cohort 1:

$p_\theta(y|x^{MRI}, x^{FDG}, z)$  Sub-cohort 2:

$p_\theta(y|x^{MRI}, x^{FDG}, x^{AYD}, z)$  Sub-cohort 3:

$p_\theta(y|x^{MRI}, x^{AYD}, z)$  Sub-cohort 4:

Further exemplary mathematical notation for the IMTL is as follows:
index i=1, . . . , $n_l$ for samples
index l=1, 2, 3, 4 for sub-cohorts
index k=1, 2, 3 for modalities
$x_i^{(kl)}$: Features in modality k for patient i in sub-cohort
$y_i^{(l)}$: Response variable for patient i in sub-cohort
$n_l$: Number of samples in sub-cohort Exemplary mathematical formulation of aspects are as follows:
Consider the joint distribution of $y_i^{(l)}$, $x_i^{(2l)}$, and $x_i^{(3l)}$ given $x_i^{(1l)}$ to be multivariate normal:
$(y_i^{(l)}, x_i^{(2l)}, x_i^{(3l)})|x_i^{(1l)} \sim MVN(\mu(x_i^{(1l)}), \Sigma)$.
$\mu(\cdot)$ is a vector function of covariates, $\Sigma$ is the covariance matrix.

$\mu(x_i^{(1l)}) = (x_i^{(1l)}\beta_1 + \beta_0, x_i^{(1l)}A_2 + b_2, x_i^{(1l)}A_3 + b_3)$ $$\Sigma = \begin{pmatrix} \sigma_y^2 & \Sigma_{y2} & \Sigma_{y3} \\ \Sigma_{2y} & \Sigma_{22} & \Sigma_{23} \\ \Sigma_{3y} & \Sigma_{32} & \Sigma_{33} \end{pmatrix}$$

Let $\Theta = (\Sigma, \beta_1, \beta_0, A_2, b_2, A_3, b_3)$ contain all the unknown parameters.

The negative log-likelihood function:

$$l(\Theta) = n\log|\Sigma| + \sum_{l=1}^{4}\sum_{i=1}^{n_l} \left(y_i^{(1)} - x_i^{(1l)}\beta_1 - \beta_0, x_i^{(2l)} - x_i^{(1l)}A_2 - b_2, x_i^{(3l)} - x_i^{(1l)}A_3 - b_3\right)$$

$$\Sigma^{-1}\left(y_i^{(1)} - x_i^{(1l)}\beta_1 - \beta_0, x_i^{(2l)} - x_i^{(1l)}A_2 - b_2, x_i^{(3l)} - x_i^{(1l)}A_3 - b_3\right)^T$$

Because of the missing modality, Expectation-Maximization (EM) is used $$\text{E-step: Derive } Q(\Theta|\Theta^{(t)}) = E_{x^{mis}|x^{obs}, \Theta^{(t)}}\left[l(\Theta)|x^{obs}, y^{obs}, \Theta^{(t)}\right]$$

$$\text{M-step: } \Theta^{(t+1)} = \arg\max_\Theta Q(\Theta|\Theta^{(t)})$$

The E-step 421 computes expectations of missing modalities and may accommodate mixed variable types by EP approximations. E step can be simplified as the conditional expectation of missing modality. An exemplary E-step in an exemplary EM algorithm is as follows:

$$\tilde{x}_i^{(24)} = E\left[x_i^{(24)}|x_i^{(14)}, x_i^{(34)}, y_i^{(4)}, \Theta^{(t)}\right] =$$

$$x_i^{(14)}\beta_1^{(t)} + \beta_0^{(t)} + (\Sigma_{2y}^{(t)}, \Sigma_{23}^{(t)})\begin{pmatrix} \sigma_y^{(t)2} & \Sigma_{y3}^{(t)} \\ \Sigma_{3y}^{(t)} & \Sigma_{33}^{(t)} \end{pmatrix}^{-1}\begin{pmatrix} y_i^{(4)} - x_i^{(14)}\beta_1^{(t)} - \beta_0^{(t)} \\ x_i^{(34)} - x_i^{(14)}A_3^{(t)} - b_3^{(t)} \end{pmatrix}.$$

$$E\left[(x_i^{(24)})^T x_i^{(24)}|x_i^{(14)}, x_i^{(34)}, y_i^{(4)}, \Theta^{(t)}\right] = (\tilde{x}_i^{(24)})^T \tilde{x}_i^{(24)} + \Sigma_{22|3y}^{(t)},$$

$$\Sigma_{22|3y}^{(t)} = \Sigma_{22}^{(t)} - (\Sigma_{2y}^{(t)}, \Sigma_{23}^{(t)})\begin{pmatrix} \sigma_y^{(t)2} & \Sigma_{y3}^{(t)} \\ \Sigma_{3y}^{(t)} & \Sigma_{33}^{(t)} \end{pmatrix}^{-1}\begin{pmatrix} \Sigma_{y2}^{(t)} \\ \Sigma_{32}^{(t)} \end{pmatrix}$$

The M-step 422 maximizes expected sum of likelihoods and may solve non-convex optimization by flexible AO algorithm. M step can be simplified as least square (LS) estimates. An exemplary M-step in an exemplary EM algorithm is as follows:

$$\begin{cases} \begin{pmatrix}\beta_0^{(t+1)}\\ \beta_1^{(t+1)}\end{pmatrix} = \left(\sum_{l=1}^{4}\sum_{i=1}^{n_l}(1, x_i^{(1l)})^T(1, x_i^{(1l)})\right)^{-1}\sum_{l=1}^{4}\sum_{i=1}^{n_l}(1, x_i^{(1l)})^T y_i^{(l)} \\ \begin{pmatrix}b_2^{(t+1)}\\ A_2^{(t+1)}\end{pmatrix} = \left(\sum_{l=1}^{4}\sum_{i=1}^{n_l}(1, x_i^{(1l)})^T(1, x_i^{(1l)})\right)^{-1}\sum_{l=1}^{4}\sum_{i=1}^{n_l}(1, x_i^{(1l)})^T \tilde{x}_i^{(2l)} \\ \begin{pmatrix}b_3^{(t+1)}\\ A_3^{(t+1)}\end{pmatrix} = \left(\sum_{l=1}^{4}\sum_{i=1}^{n_l}(1, x_i^{(1l)})^T(1, x_i^{(1l)})\right)^{-1}\sum_{l=1}^{4}\sum_{i=1}^{n_l}(1, x_i^{(1l)})^T \tilde{x}_i^{(3l)} \end{cases}$$

-continued $$\Sigma^{(t+1)} = \frac{1}{n}\left\{\begin{pmatrix}\sum_{l=1}^{4}\sum_{i=1}^{n_l}(z_i^{(l)})^T z_i^{(l)} + n_4\begin{pmatrix}0 & 0 & 0\\ 0 & \Sigma_{22|3y}^{(t)} & 0\\ 0 & 0 & 0\end{pmatrix}+\\ n_2\begin{pmatrix}0 & 0 & 0\\ 0 & 0 & 0\\ 0 & 0 & \hat{\Sigma}_{33|2y}^{(t)}\end{pmatrix}+n_1\begin{pmatrix}0 & 0 & 0\\ 0 & \Sigma_{22|y}^{(t)} & \Sigma_{23|y}^{(t)}\\ 0 & \Sigma_{32|y}^{(t)} & \Sigma_{33|y}^{(t)}\end{pmatrix}\end{pmatrix}\right\}$$

An exemplary formulation for the prediction for each sub-cohort is as follows:

$$\hat{y}_{i^*} = x_{i^*}^{(11)}\hat{\beta}_1 + \hat{\beta}_0, \text{ if } i^* \in \text{sub-cohort 1};$$

$$\hat{y}_{i^*} = x_{i^*}^{(12)}(\hat{\beta}_1 - \hat{A}_2\hat{\Sigma}_{22}^{-1}\hat{\Sigma}_{2y}) + x_{i^*}^{(22)}\hat{\Sigma}_{22}^{-1}\hat{\Sigma}_{2y} + (\hat{\beta}_0 - \hat{b}_2\hat{\Sigma}_{22}^{-1}\hat{\Sigma}_{2y}), \text{ if } i^* \in \text{sub-cohort 2};$$

$$\hat{y}_i* = x_{i^*}^{(13)}\left(\hat{\beta}_1 - (\hat{A}_2, \hat{A}_3)\begin{pmatrix}\hat{\Sigma}_{22} & \hat{\Sigma}_{23}\\ \hat{\Sigma}_{32} & \hat{\Sigma}_{33}\end{pmatrix}^{-1}\begin{pmatrix}\hat{\Sigma}_{2y}\\ \hat{\Sigma}_{3y}\end{pmatrix}\right) +$$

$$(x_{i^*}^{(23)}, x_{i^*}^{(33)})\begin{pmatrix}\hat{\Sigma}_{22} & \hat{\Sigma}_{23}\\ \hat{\Sigma}_{32} & \hat{\Sigma}_{33}\end{pmatrix}^{-1}\begin{pmatrix}\hat{\Sigma}_{2y}\\ \hat{\Sigma}_{3y}\end{pmatrix} + \left(\hat{\beta}_0 - (\hat{b}_2, \hat{b}_3)\begin{pmatrix}\hat{\Sigma}_{22} & \hat{\Sigma}_{23}\\ \hat{\Sigma}_{32} & \hat{\Sigma}_{33}\end{pmatrix}^{-1}\begin{pmatrix}\hat{\Sigma}_{2y}\\ \hat{\Sigma}_{3y}\end{pmatrix}\right), \text{ if } i^* \in \text{sub-cohort 3};$$

$$\hat{y}_{i^*} = x_{i^*}^{(14)}(\hat{\beta}_1 - \hat{A}_3\hat{\Sigma}_{33}^{-1}\hat{\Sigma}_{3y}) + x_{i^*}^{(34)}\hat{\Sigma}_{33}^{-1}\hat{\Sigma}_{3y} + (\hat{\beta}_0 - \hat{b}_3\hat{\Sigma}_{33}^{-1}\hat{\Sigma}_{3y}), \text{ if } i^* \in \text{sub-cohort 4};$$

A similar procedure may be used to a classification model.

According to one embodiment, a fisher information performance is used. The larger the fisher information, the smaller the variance of the estimator. The fisher information under IMTL is larger than separate modeling (SM). Aspects of the fisher information performance are as follows:

The maximum likelihood estimator has the following property:

$$\sqrt{n}(\hat{\theta}-\theta_0) \rightarrow N(0, I^{-1})$$

I is the fisher information.
Consider two modality IMD structure with modality 2 having missing data:

$$(y_i^{(I)}, x_i^{(2I)}) \mid x_i^{(1I)} \sim MVN(\mu(x_i^{(1I)}), \Sigma),$$

$$\Sigma = \begin{pmatrix}\sigma_{yy} & \sigma_{y2}\\ \sigma_{2y} & \sigma_{22}\end{pmatrix} \text{ and } \Omega \triangleq \Sigma^{-1} = \begin{pmatrix}\theta_{yy} & \theta_{y2}\\ \theta_{2y} & \theta_{22}\end{pmatrix}.$$

Let $I_{IMTL}(\theta_{ij})$ be the Fisher information for each element in $\Omega$ under IMTL. Let $I_{SM}(\theta_{ij})$ and be the Fisher information under SM, respectively. Then, $I_{IMTL}(\theta_{ij}) > I_{SM}(\theta_{ij})$, if the following condition holds, $$\frac{-n_1 + 2p_1 + \sqrt{(n_1 - 2p_1)^2 + 4n_1 p_1}}{4p_1} < \frac{\sigma_{2y}^2}{\sigma_{22}\sigma_{yy}},$$

where $n_1$ is the sample size of sub-cohort 1 (i.e., the sub-cohort with only modality 1 available) and $p_1$ is number of features of modality 1. $I_{IMTL}(\theta_{ij}) > I_{SM}(\theta_{ij})$ shows the superiority of IMTL over Separate Modeling (SM). The condition $$\frac{-n_1 + 2p_1 + \sqrt{(n_1 - 2p_1)^2 + 4n_1 p_1}}{4p_1} < \frac{\sigma_{2y}^2}{\sigma_{22}\sigma_{yy}}$$

identifies the negative transfer condition for IMTL, avoiding the drawback of transfer learning.

Figure 9:
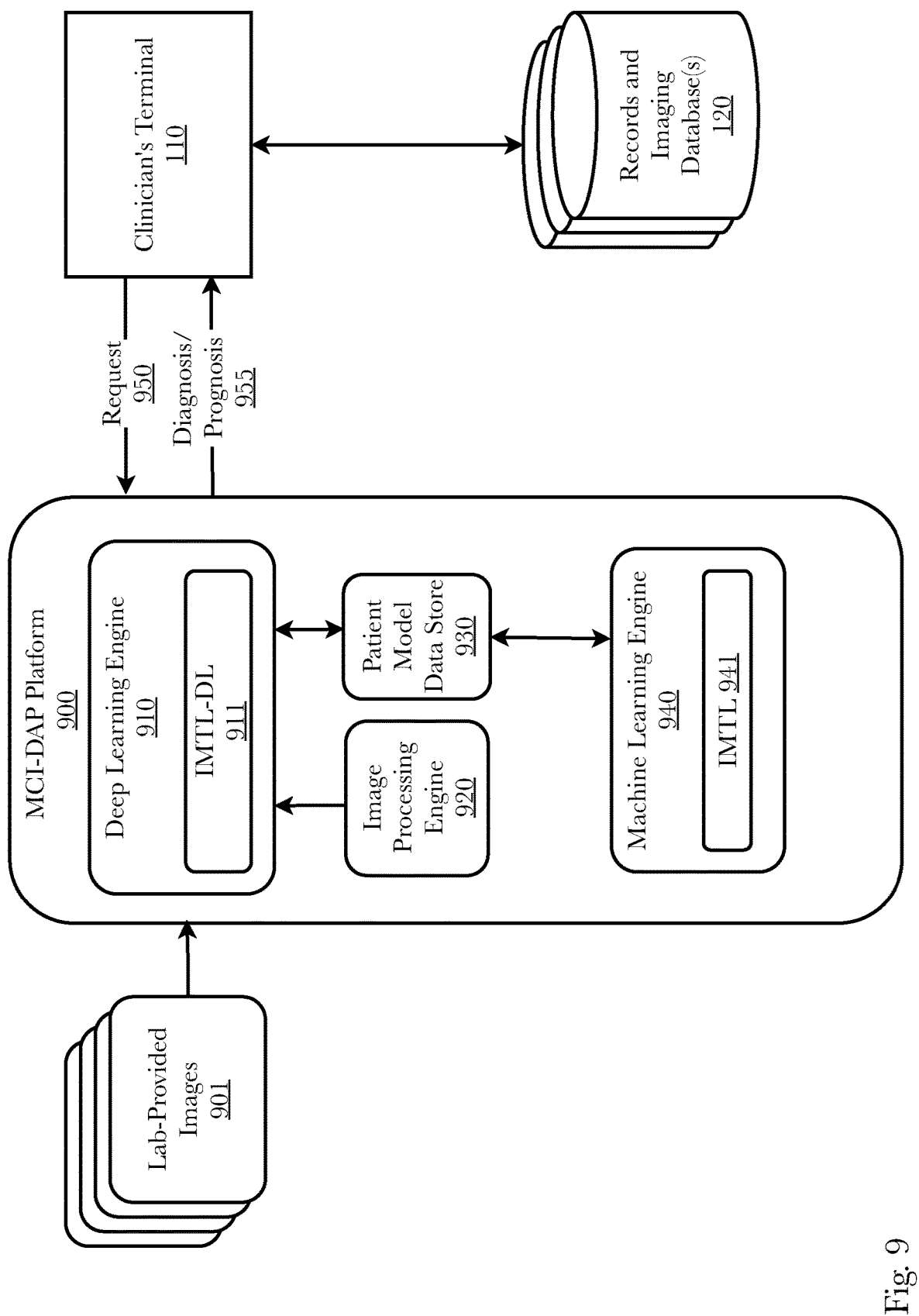
FIG. 9 is a block diagram illustrating an exemplary system architecture for diagnostics and prognostics of mild cognitive impairment using deep learning, according to an embodiment.

FIG. 9 is a block diagram illustrating an exemplary system architecture for a mild cognitive impairment—diagnostic and prognostic (MCI-DAP) platform 900. According to various embodiments, MCI-DAP platform may be a specifically configured embodiment of (MCI-DAP) server 100. According to various embodiments, a mild cognitive impairment diagnostic and prognostic (MCI-DAP) platform 900 comprises a machine learning engine 940 utilizing an incomplete multi-modality transfer learning algorithm (IMTL) 941, a deep learning engine 910 utilizing the IMTL 941 integrated with a deep learning algorithm (IMTL-DL) 911, a patient model data store 920 which stores learned models and associated data, and an image processing engine 920 which prepares images 901 for machine and deep learning applications. The server may be communicatively coupled to a clinician's terminal 110 and a records and imaging database(s) 120, whereby a clinician may request 950 to receive predictions 955 from the MCI-DAP platform 900 which retrieves patient data 950 from one or more records and imaging databases 120 and outputs a prediction 955. The records and imaging database 120 is also typically networked with radiology and other hospital departments such that a patient's image data is co-located with other medical information. Furthermore, the records and imaging database 120 as disclosed herein is merely exemplary and represents any digital or analog data store that holds image data and other medical data pertaining to patients.

The machine learning engine 940 employing the incomplete multi-modality transfer learning algorithm (IMTL) 941 does not require filling in the modality-wise missing data. With an end goal to train an ML model for each patient sub-cohort, IMTL 941 couples the processes of training the sub-cohort-wise models together using an iterative EM algorithm to allow information transfer between the models. This is different from SM of each sub-cohort, with benefit of augmenting the sample size of each sub-cohort using the transferred information served as virtual samples, and thus producing estimators for the model coefficients with less variance—a nice statistical property leading to less variability (thus robustness) of using the model to make a diagnosis/prognosis. Mathematical details are disclosed in FIG. 4.

The deep learning engine 910 is responsible for the training, deployment, and maintenance of deep learning models developed to make predictions on prognosis and diagnosis of mild cognitive impairment and Alzheimer's Disease for a given patient based on the patient's health record and any available imaging data. Deep learning engine 910 integrates one or more deep learning algorithms with IMTL 941 forming an IMTL-DL algorithm 911. According to various embodiments, the deep learning algorithm may be a deep neural network. In some embodiments, the deep neural network may be a recurrent neural network, a convolutional neural network, various other types of deep learning algorithms, or some combination of deep learning algorithms. According to the embodiment, deep learning engine 910 may also perform various data processing tasks to train the deep learning algorithms therein. For example, deep learning engine 910 may receive a dataset, clean and transform it as necessary in order to be used as input into the one or more deep learning algorithms. Furthermore, deep learning engine 910 can be segregate a dataset or multiple datasets into a training dataset and a test dataset for algorithm training purposes.

According to some embodiments deep learning engine 910 may train one or more deep learning algorithms in a "training environment", similar to the offline model training described in FIG. 3, wherein the one or more deep learning algorithms may be trained in a feedback loop. In the feedback loop, the algorithm is fed training input data, the output of the algorithm is compared against the expected output (contained in training dataset), and the comparison results is used as feedback to drive algorithmic updates such as, for example, parameter and hyperparameter optimization, and training dataset adjustments. A test dataset may be fed as input into a deep learning algorithm in the training environment, wherein the test dataset represents "new" data the algorithm has never processed before and the outputs based on the test dataset may be compared against the expected outputs. If the test was successful (e.g., criteria for success was met), then the deep learning algorithm has been fully trained into a model that can make accurate predictions. This trained model may be deployed to a "production environment" where it can begin receiving patient records and imaging data and make predictions on prognosis and diagnosis. The trained model may be sent to patient model data store 930 for storage and retrieval as needed. A clinician 110 may make a request 950 to platform 900 wherein the request contains patient imaging data, and the IMTL-DL can process the patient imaging data the IMTL-DL to create a patient specific model that outputs patient specific predictions 955 which are received by the clinician at his or her terminal 110.

According to various embodiments, MCI-DAP platform 900 may be offered as a service to clinics and hospitals which provides a plurality of use cases including, but not limited to: computer aided diagnosis (CAD) to predict Alzheimer's Disease (AD), diagnosis of MCI due to AD, and prognosis of MCI due to AD; drug development, wherein the features used by the machine and deep learning algorithms may be used to identify potential attack vectors for potential drugs to treat MCI and/or AD; imaging acquisition augmentation; and a decision support system, wherein the predictions output by MCI-DAP platform 900 may be used a single data point for a patient or physician to use when seeking or providing medical care.

According to various embodiments, MCI-DAP platform 900 may be configured to make predictions about Alzheimer's Disease (AD) using non-imaging data. In some embodiments, non-imaging data may comprise movement and/or positional data of a patient as gathered by one various sensor systems (e.g., accelerometers, radar, LiDAR, gyroscopes, force sensors, pressure sensors, cameras, etc.) and fed into machine and deep learning algorithms to make predictions about AD progression.

Figure 10:
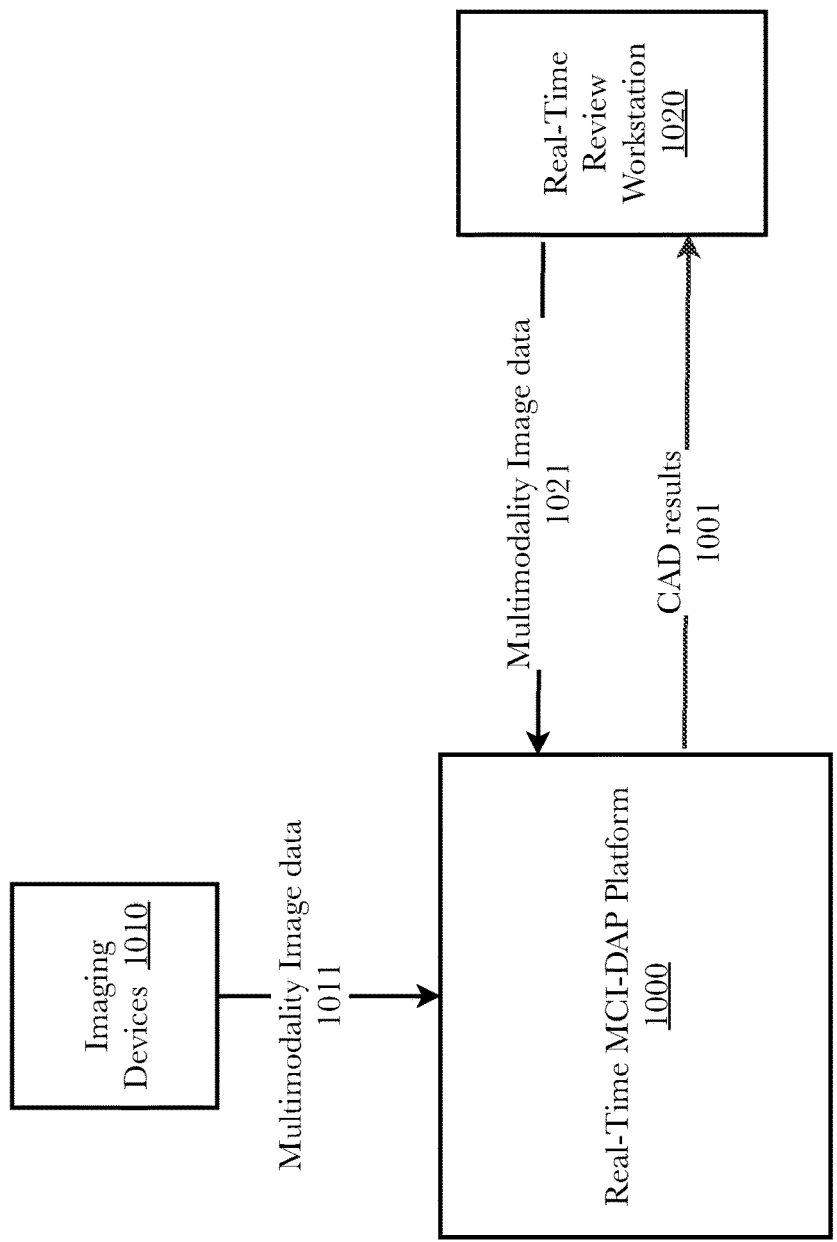
FIG. 10 is a block diagram illustrating an exemplary arrangement of the MCI-DAP platform configured for real-time image processing, according to an aspect.

FIG. 10 is a block diagram illustrating an exemplary arrangement of the MCI-DAP platform configured for real-time image processing, according to an aspect. According to the aspect, the MCI-DAP platform is be configured to operate as a service that provides real-time diagnostic and prognostic predictions on received patient data. The arrangement comprises a real-time MCI-DAP platform 1000 that receives requests for predictions comprising patient data (e.g., patient records) and multimodality image data 1021, 1011 from a real-time review workstation 1020 and/or from imaging devices 1010. Not shown, but present in the arrangement, is a communication network that connects real-time MCI-DAP platform 1000 with real-time review workstation 1020 and imaging devices 1010 to facilitate bi-directional communication between the components. According to some embodiments, the communications network may be a local area network (LAN) wherein the real-time MCI-DAP platform 1000, review workstation 1020 and imaging devices 1010 may be disposed in close proximity and connected to each other over a wired connection (e.g., Ethernet protocol). In other embodiments, the communication network may be a wide or wireless area network (WAN) wherein the real-time MCI-DAP platform 1000, review workstation 1020, and imaging devices are remote from each other and connected to each other over an appropriate network. In other embodiments, real-time MCI-DAP platform 1000 is a cloud-based service that is communicatively coupled to the review workstation 1020 and imaging devices 1010 over a network connection such as the Internet.

Real-time review workstation 1020 may be similar to or a specifically configured version of clinician's terminal 110, referring to FIG. 1. In various embodiments, real-time review workstation 1020 may comprise at least a computing device comprising at least one processor and possessing a memory, and may further comprise a display for reviewing patient records and predictions received from real-time MCI-DAP platform 1000, and other input/output devices (e.g., keyboard, mouse, camera, microphone, etc.).

In operation, image data 1021, 1011 are automatically sent to real-time MCI-DAP platform 1000 wherein one or more machine and deep learning models will be used to process the image data, and the computer aided diagnosis (CAD) results 1001 (i.e., model predictions) are automatically sent to the clinician at real-time review workstation 1020.

Figure 11:
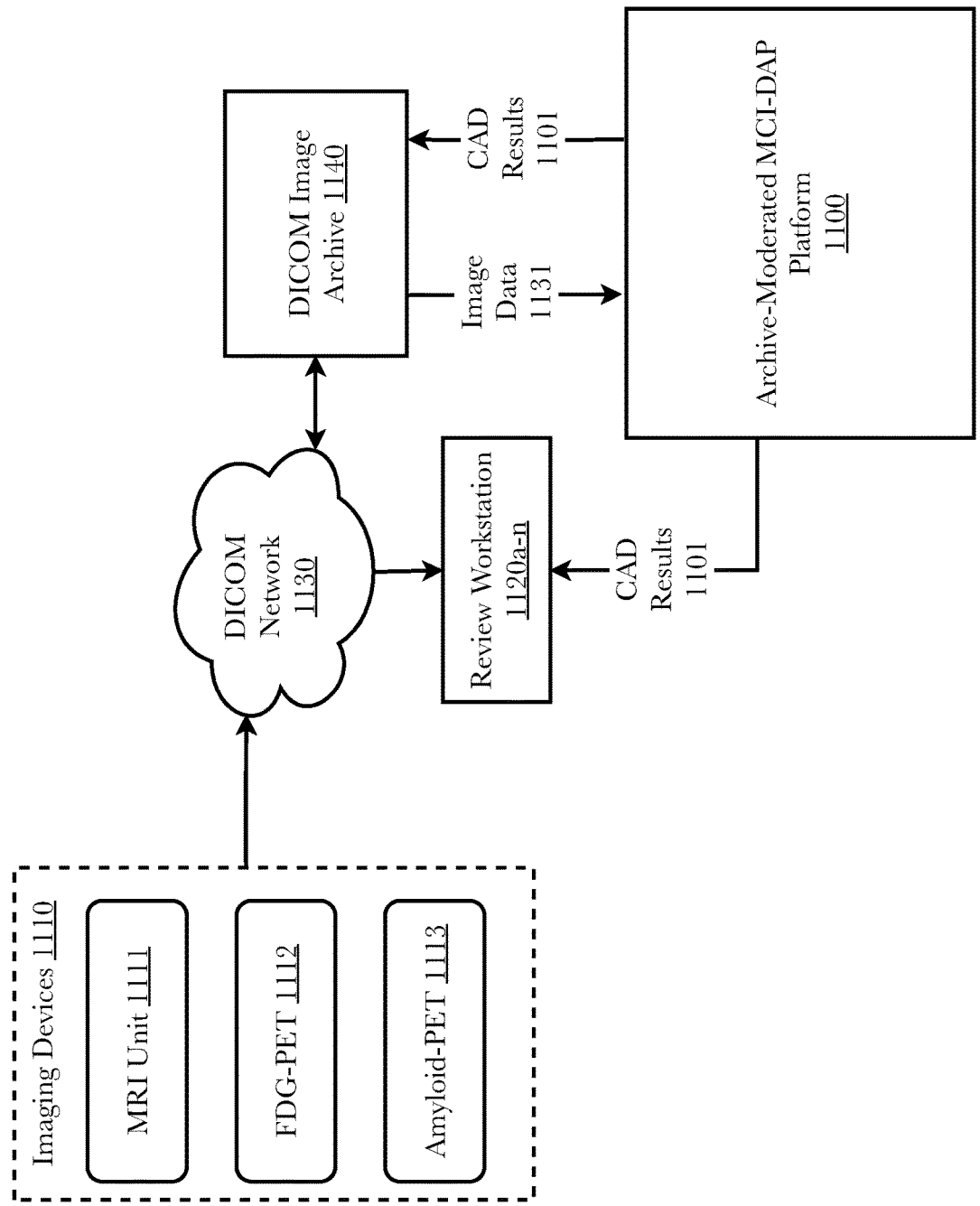
FIG. 11 is a block diagram illustrating an exemplary arrangement of the MCI-DAP platform configured as an archive-moderated system, according to an aspect.

FIG. 11 is a block diagram illustrating an exemplary arrangement of the MCI-DAP platform configured as an archive-moderated system, according to an aspect. According to the aspect, the MCI-DAP platform is be configured to operate as a service that provides archive-moderated diagnostic and prognostic predictions on received patient data. The arrangement comprises a plurality of various imaging devices 1110 which send, via a DICOM network 1130, image data directly to one or more review workstations 1120a-n and a DICOM image archive 1130 for storage. DICOM network 1130 is a data network connecting DICOM-compliant devices (i.e., imaging devices 1110) within a medical institution or department. In some embodiments, DICOM network 1130 is configured as a local area network (LAN), and thus a typical network interface such as an Ethernet interface is used for connection and communication between devices on DICOM network 1130. DICOM image archive 1140 is a DICOM compliant device that can store a plurality of imaging data. In some embodiments, DICOM image archive 1140 can be a specifically configured computer server with at least one processor, a memory, and a non-transitory data storage system. In other embodiments, DICOM image archive 1140 may be a specifically configured datastore or database such as a relational database or data warehouse.

According to the aspect, imaging devices 1110 may comprise the following devices, but is not necessarily limited to only these devices, an MRI unit 1111, a FDG-PET unit 1112, and an Amyloid-PET unit 1113. Each of these imaging devices 1110 may provide patient images from different modalities, which can be used as input into the one or more machine and deep learning models operating within archive-moderated MCI-DAP platform 1100 to make predictions on diagnosis and prognosis of MCI due to AD.

Review workstation 1120*a-n* may be similar to or a specifically configured version of clinician's terminal 110, referring to FIG. 1. In various embodiments, review workstation 1120 may comprise at least a computing device comprising at least one processor and possessing a memory, and may further comprise a display for reviewing patient records and predictions received from archive-moderated MCI-DAP platform 1100, and other input/output devices (e.g., keyboard, mouse, camera, microphone, etc.).

In operation, a physician at one of the review workstations 1120*a-n* receives patient image data and can submit a request for archive-moderated MCI-DAP platform 1110 to process the patient image data to generate a prediction. DICOM image archive 1130 receives the request from review workstation 1120*a-n*, retrieves image data associated with the patient of interest, and sends the retrieved image data 1131 to archive-moderated MCI-DAP platform 1110 which processes the received data and automatically sends its CAD results 1101 (i.e., predicted diagnosis and/or prognosis) to both review workstation 1120*a-n* where a physician can review the results and present them to the patient and to DICOM image archive 1130 for storage.

In this arrangement, it is possible for DICOM image archive 1140 to connect with twenty-five output destinations (i.e., archive-moderated MCI-DAP platform 1110, review workstations 1120*a-n*) and can store at least six possible DICOM objects. The six DICOM objects may comprise secondary capture, gray scale presentation state, stand-alone curve (group 5000), embedded curve (group 5000), stand-alone overlay (group 6000), and embedded overlay (group 6000).

FIGS. 12A and 12B describe an exemplary configuration of an incomplete multi-modality transfer learning algorithm integrated with a deep learning algorithm (IMTL-DL). With an end goal to train a DL model for each patient sub-cohort, FIG. 12A describes an exemplary head architecture in reverse and FIG. 12B describes an exemplary backbone architecture in reverse. A legend 1200 is provided and referenced for ease of readability purposes and to simplify the exemplary drawing.

According to this aspect, the deep learning algorithm is a reverse multi-task recurrent neural network (RNN). This diagram is another example of an incomplete multi-modality image dataset that can be modeled by IMTL, modeled in FIG. 1. A plurality of sub-cohorts are utilized to train an IMTL algorithm to estimate modality data in order to output a complete dataset comprising actual patient modality data and estimated data. The output data from the head architecture is used as input into the deep learning algorithm in order to train it to make predictions for prognosis and diagnosis.

Sub-Cohort 1 1220 represents a partially available (i.e., incomplete) imaging modality consisting of patients with only volumetric MRI 1201 imaging data available. In this sub-cohort, MRI training images with a dimension of 91×109×91 are passed through deep learning layers to train the deep learning algorithm. For example, an image is first passed through a Conv3D, 3×3×3, ReLu 1205 layer. The three-dimensional convolutional neural network layer with filter size 3×3×3 extracts features from the image, resulting in a feature map that can be fed to the next layer to extract higher-level features. This layer implements a rectified linear activation function unit, or ReLu, in order to use stochastic gradient descent with backpropagation of errors to train the deep neural network. The activation function looks and acts like a linear function but is a nonlinear function allowing complex data relationships to be learned while providing more sensitivity to the activation sum input and avoiding easy saturation. This technique permits development of very deep neural networks. A dataset consisting of feature maps produced only from MRI imaging data is passed through a Conv3D, 3×3×3, ReLu 1205 layer and then through a Max Pooling 1207 layer. The pooling operation calculates the maximal value in each patch of each feature map, resulting in pooled feature maps highlighting the maximal presence of different features to identify patterns across the dataset, resulting in 45×54×45 MRI imaging data. The sub-cohort's deep learning algorithm results in an imaging dataset comprised of the sub-cohort's modalities (here, MRI only) and will undergo transfer learning across other sub-cohort algorithm datasets as described in FIG. 1 and FIG. 4, modified to work with a deep learning algorithm. The result of this transfer learning is a unified data set which can be fed into the backbone architecture FIG. 12B to produce prognosis and diagnosis output. For example, outputs are transformed to a new dimension of 45×54×45 and passed through iterative Conv3D, 3×3×3,ReLu 1205 layers, in this case passing through twice. The output is transformed to a dimension of 22×27×22 and then passed through a Max Pooling 1207 layer, two Conv3D, 3×3×3, ReLu 1205 layers, and another Max Pooling 1207 layer. The output is transformed to a dimension of 11×13×11. Once the convolutional operations are completed, the algorithm will Flatten 1209 the feature and feed the result to Fully Connected 1210 layer. The layer applies a linear transformation to the input vector through a weights matrix to produce an output value of either 0 or 1, wherein the output corresponds to a prediction of whether the patient, based on the input patient data, has MCI (e.g., diagnosis) or whether the patient shows signs of potential MCI (e.g., prognosis).

Sub-Cohort 2 1230 represents a partially available imaging modality consisting of patients with both volumetric MRI 1201 and volumetric FDG-PET 1203 imaging modalities available. For example, in this sub-cohort, the MRI and FDG-PET training images with dimensions of 91×109×91 are passed separately through a Conv3D, 3×3'3, ReLu 1205 layer into separate datasets comprising the outputs. These datasets are combined into one dataset and passed through a Conv3D, 1×1×1 1206 layer. The three-dimensional convolutional neural network layer has a filter size of 1×1×1, reducing the number of operations and the computational needs to increase efficiency. The IMTL algorithm fuses the output from the available modalities into a dataset of Fused Data 1208, in this case MRI and FDG-PET modalities, using representation learning 1204 to articulate a straight and obvious training target for the multi-modality dataset. The algorithm learns the representation, determining a data representation of the feature maps, the distance function, and the similarity function that determines how the predictive model will perform. Representation learning works by reducing high-dimensional data to low-dimensional data. The algorithm examines the combined dataset for traits and representations, discovering patterns and anomalies while also providing a better understanding of the data's overall behavior. Just like Sub-Cohort 1, this sub-cohort's dataset consisting of multi-modality feature maps from both MRI and FDG-PET modalities is passed through a Conv3D, 3×3×3, ReLu 1205 layer and then through a Max Pooling 1207 layer, with the output transformed to a dimension of 45×54×45. The output is then used as input to train the deep learning algorithm FIG. 12B.

Sub-Cohort 3 1240 and Sub-Cohort 4 1250 exemplify other multi-modality combinations used to train the IMTL-DL algorithm. These sub-cohorts use the same processes of Sub-Cohort 2 1230 applied to the modalities within the sub-cohort, where Sub-Cohort 3 1240 comprises information where only volumetric MRI 1201, FDG-PET 1202, and Amyloid-PET 1203 imaging modalities are available and where Sub-Cohort 4 1250 comprises only volumetric MRI 1201 and Amyloid-PET 1203 modalities. These sub-cohorts are exemplary and do not represent the full scope of modalities. Other modalities may be considered such as FLAIR, DTI, fMRI, and Florbetapir-PET. Additional sub-cohorts may exist comprising medical imaging data selected from the group of MRI, FDG-PET, amyloid-PET, FLAIR, DTI, fMRI, Florbetapir-PET, and any combination thereof.

The extended IMTL-DL with deep learning is capable of processing longitudinal images. For example, at an initial appointment, an MRI image may be taken. At a follow-up appointment X number of months later, a second MRI image may be taken for the same patient. Both or more images can be fed into the IMTL-DL in order to make diagnosis and prognosis predictions based on the longitudinal data. When imaging data is available at multiple time points (e.g., both baseline and a follow-up visit), incorporating the changes in imaging features in IMTL-DL improves the diagnostic/prognostic accuracy. The extended IMTL-DL can further process longitudinal data for individual patients to track rate of change related to MCI or AD between visits and predict degradation.

Detailed Description of Exemplary Aspects

Figure 5:
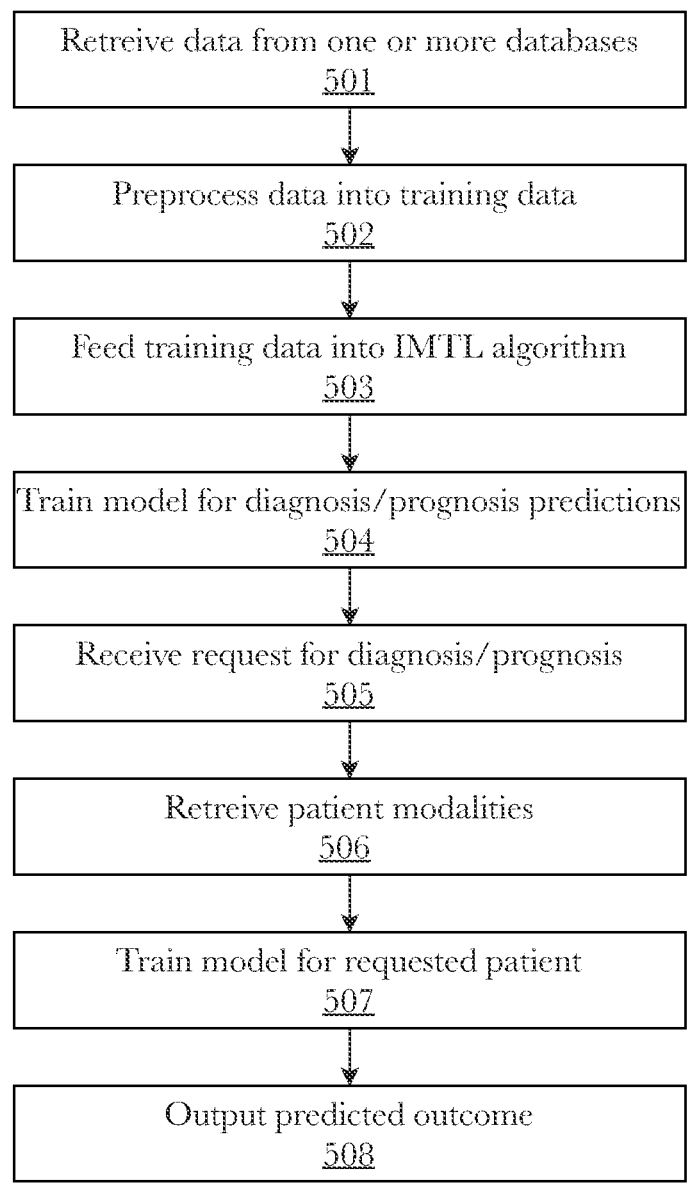
FIG. 5 is a flow diagram illustrating an exemplary method for diagnostic and prognostic predictions using a mild cognitive impairment—diagnostic and prognostic (MCI-DAP) server, according to one aspect.

FIG. 5 is a flow diagram illustrating an exemplary method for diagnostic and prognostic predictions using a mild cognitive impairment—diagnostic and prognostic (MCI-DAP) server, according to one aspect. The MCI-DAP Server comprises an "offline model training using CLPAMD" module and an "online clinical decision making" module. According to one embodiment, the offline module is run at the backend. It takes in a CPAMD of n existing patients from one or more data sources 501, collected at time t1 (e.g., baseline),—if data is not ready, it is preprocessed 502—and fed 503 into a multitask learning algorithm to produce a diagnostic/prognostic model for each patient cohort that has the same available imaging modalities. Next, the offline module combines the t1 model for each patient cohort and the LPAMD for the same cohort collected at t2 (e.g., six months) by transfer learning, and produces updated diagnostic/prognostic models for each cohort at t2. This process is repeated until diagnostic/prognostic models for every time point of interest are obtained 504.

The "online clinical decision making" module is the frontend that a clinician interacts with. Specifically, when seeing a new patient for the first time (i.e., baseline), the clinician will feed the patient's available imaging modalities into the online module, or in another embodiment the clinicians will request a diagnosis/prognosis 505 in which the MCI-DAP Server retrieves all available patient modalities 506. The online module will first find a patient cohort in training that matches with the new patient's available imaging modalities. Then, it will use the corresponding training model 507 of that cohort to produce a diagnostic and prognostic result for the new patient 508. At a follow-up visit (e.g., six months) for the same patient, the clinician will feed the patient's newly collected data from the follow-up visit into the online module. The online module will first find a matching cohort in training at the same follow up time interval, and then use the corresponding training model 507 to produce an updated diagnostic and prognostic result for the patient 508.

Figure 6:
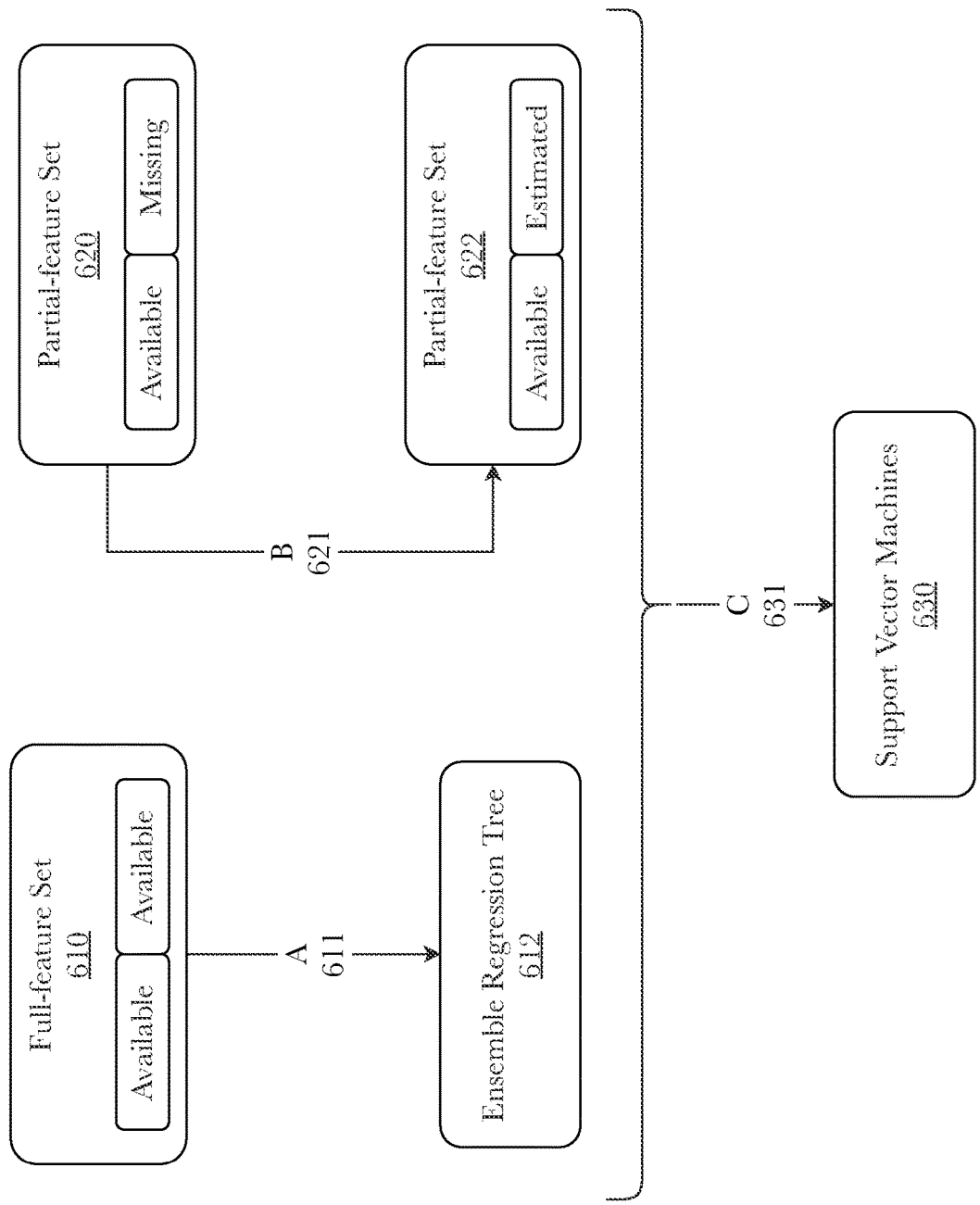
FIG. 6 is a block diagram illustrating an exemplary workflow to estimate missing biomarkers as one aspect of the transfer learning model.

FIG. 6 is a block diagram illustrating an exemplary workflow to estimate missing biomarkers as one aspect of the transfer learning model. Ensemble methods 612 are learning algorithms that construct a set of predictive models and then predict new data points by taking a (weighted) vote of their predictions. Boosting is a machine learning ensemble meta-algorithm for primarily reducing bias and also variance. It involves incrementally building an ensemble by training each new model instance to emphasize the training instances that previous models have miss classified. According to one embodiment, boosting of regression tree is used because of its advantages on dealing with nonlinear and large dimension datasets with categorical features. In one experiment conducted by the inventors, a regression ensemble of 50 regression trees is implemented using least square boost (LSBoost) to estimate missing values. For each single regression tree, the maximum split number is set to be 4 to avoid overfitting. After training with "full-feature" set 610, the ERT is applied to estimate the missing elements in the "partial-feature" instances 620/622 to make up the full dataset (A 611+B 621) which is then used to develop (C 631) the SVM classifier 630, discussed in the next section.

Support vector machine (SVM) is a classifier that constructs set of hyperplanes in a high dimensional space for classification. According to one embodiment, an SVM 630 with Gaussian kernel is implemented. To ensure a good performance of SVM, 9 features (age, ADAS-Cog, 5 biomarkers from MRI and 2 biomarkers from FDG-PET) are selected due to the fact that they are numerical and high correlations with AD disease as predictors. Because of an imbalanced dataset (55 positive vs. 91 negative responses), different weights are assigned to two classes of instances in the SVM model. In addition, different weights are assigned to instances with estimated values and instances with true values. Specifically, each instance is assigned with 1 out of 4 different weights. The ratio of weights between positive and negative instance is set to be 1.65:1. The ratio of weights between true value instance and estimated value instance is 2:1, which is pre-determined according to the best performance of experiment.

Given the dataset with missing value constructed, a single SVM with ERT estimate (SVMest) is used to develop the classifier. A full-feature set is used to train an ERT to learn the relationship between full-features and partial-features. Next, the missing values of mcSUVRcere are derived from the trained ERT as estimates. Using the full-feature set and partial-feature set filled in with estimated values, an SVM classifier on due/not due to AD is developed.

Given the importance of the 18F-AV45-PET biomarker and possible unavailability of such biomarker for the patients across multiple visits, an ensemble regression tree is used to estimate this biomarker which in conjunction with other features to develop the predictive models. The results show significant improvement after estimating the missing biomarker compared with competing models. When the missing ratio is within the range of 20% to 60%, our proposed model has an average accuracy that 7.1% higher than the competing model and 7.4% higher in sensitivity. Facts, figures, and estimates given herein are exemplary and are given for illustrative purposes.

FIG. 7 is a block diagram illustrating an exemplary cross-sectionally partially-available multi-modality dataset and the definition of tasks 710-713. This diagram illustrates a CPAMD 720-724 for modeling using multitask learning in order to produce powerful and accurate diagnostic and prognostic models. Diagnostic and prognostic models are developed at a single time point (e.g., baseline) from a CPAMD 720-724 of n existing patients. "A suite of models" is developed to generate complementary results for clinicians to cross-reference and better inform their decisions. These models are different in their outcome measures, but they will use the same CPAMD 720-724. For diagnostic modeling, we consider the outcome variable to be binary, i.e., MCI due to AD or not due to AD. For prognostic modeling, we consider two types of outcome variables: (1) A binary outcome of conversion vs. non-conversion to AD within a certain timeframe. Multiple time points can be considered such as baseline, six months, one year, etc. (2) A survival type of outcome, i.e., the time to conversion or censoring time.

Figure 8:
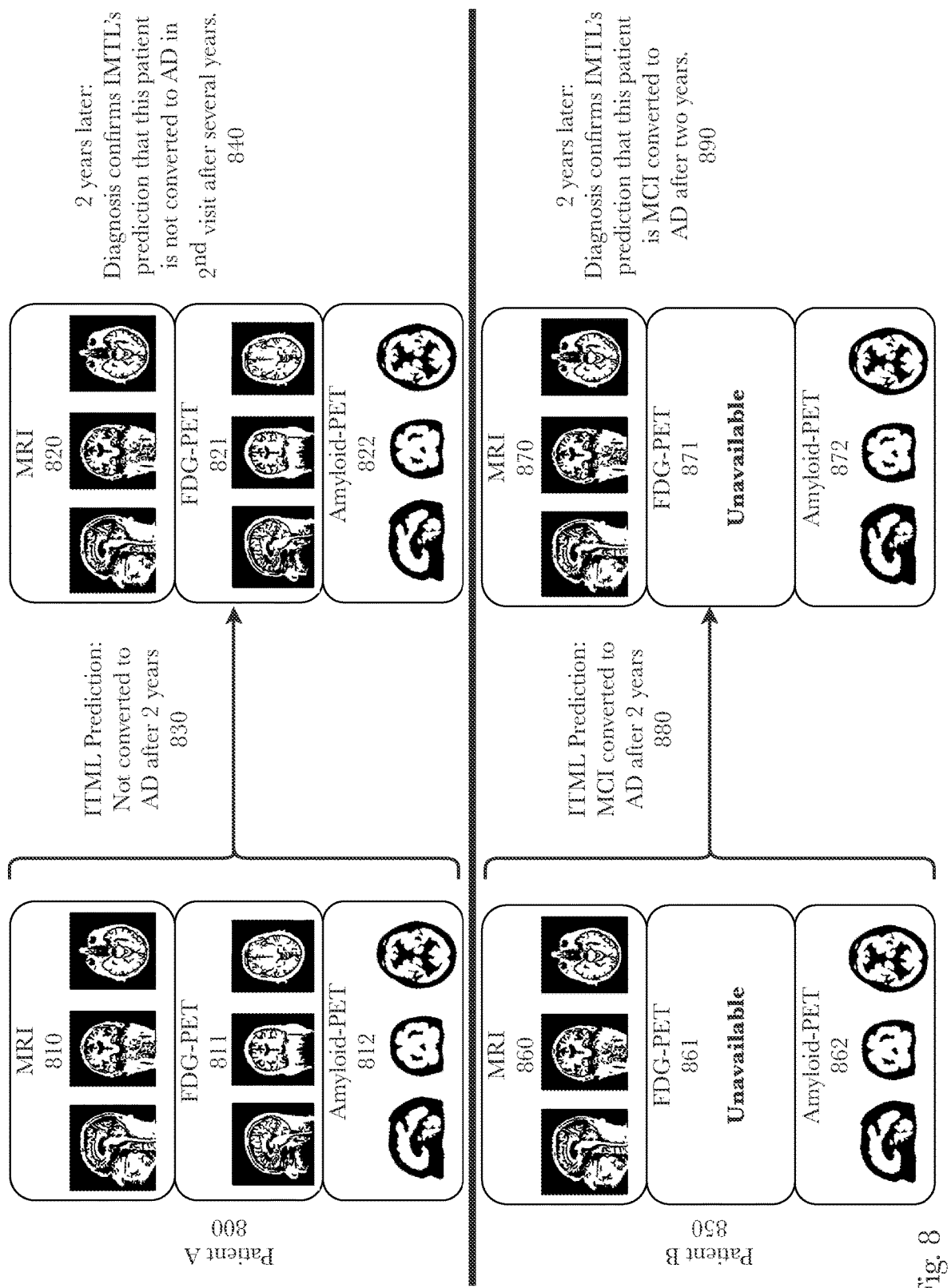
FIG. 8 is a block diagram illustrating two exemplary cases of predicting mild cognitive impairment conversion to Alzheimer's Disease.

FIG. 8 is a block diagram illustrating two exemplary cases of predicting mild cognitive impairment conversion to Alzheimer's Disease. Consider two patients: patient A 800 and patient B 850. Patient A 800 is a male of age 71. Upon visits with his medical health provider, patient A 800 receives an MRI 810, FDG-PET 811, Amyloid-PET 812. His provider then requests a diagnosis from an MCI-DAP server. The diagnosis received back is no conversion to AD after two years 830. Two years later, after a follow up visit patient A 800 receives another set of imaging 820-822 which is interpreted by a medical professional. The medical professional determines that higher amyloid deposits were not observed several years after the baseline 810-812 and similar glucose metabolism was observed between the baseline 810-812 and follow-up visit several years later. This would confirm the IMTL's algorithmic prediction 840.

Patient B 850 is a male of age 79. Upon visits with his medical health provider, patient B 850 receives an MRI 860 and an Amyloid-PET 862, but no FDG-PET due to his insurance plan. His provider then requests a diagnosis from an MCI-DAP server. The diagnosis received back is MCI conversion to AD after two years 880. Two years later, after a follow up visit patient B 850 receives another set of imaging 870, 872 (again no FDG-PET 871) which is interpreted by a medical professional. The medical professional determines that higher amyloid accumulation in the cortical brain areas is observed along with reduced glucose metabolism in the parietotemporal reg, a shrinkage of the hippocampus, and enlarged ventricles several years after the baseline 860, 862. A diagnosis is given of MCI conversion to AD after two years, which confirms the IMTL's algorithmic prediction 890.

FIG. 13 is a method diagram illustrating an exemplary workflow to produce outputs using the IMTL-DL model. This process may be performed within Deep Learning Engine 910. IMTL-DL 912 receives a full dataset 1301 of multi-modality imaging data, collected either at a single time point (i.e., at the baseline visit) or longitudinally across two or more visits. The Alzheimer's Disease Neuroimaging Initiative (ADNI) database may be used to source training data. This data is preprocessed into training data 1302 subsets to train deep learning algorithms. For Sub-Cohort 1 1220, a subset consisting of only MRI modality imaging data may be used to train the sub-cohort's specific algorithm. Similarly, a subset of ADNI data consisting of MRI and FDG-PET modality data may be used to train the Sub-Cohort 2 1230 model. Other subsets of training data may be created from available modalities separately or in any combination thereof.

The subset of training data is fed into the neural network (e.g., RMT RNN) 1303 and used to train a model for diagnosis and prognosis predictions 1304. Continuous training and re-training may take place, with updated or new datasets fed into RMT RNN 1303 to increase accuracy and efficiency of predictions by a trained model 1304. Models may be validated by applying a trained model to complete or incomplete patient modalities, such as those sourced from the Open Access Series of Imaging Studies (OASIS) data sets or the Australian Imaging, Biomarker & Lifestyle Flagship Study of Ageing (AIBL) study. Such source datasets with known outcomes may be curated and passed through the IMTL-DL in order to validate the outputs. Cross validation across sub-cohort models and transfer learning may be further applied for training and verification. Once a model has been trained satisfactorily, it can be applied to patient modalities. MCI-DAP Server 100 can receive a request for diagnosis/prognosis 1305 from Clinician's Terminal 110. Patient modalities can be retrieved 1306 from Lab-Provided Images 901 or from Records and Imaging Database(s) 130 and fed into a trained model 1307 to output a predicted outcome 1308 for prognosis and diagnosis 955 and provided to Clinician's Terminal 110. Predictions and actual patient outcomes may be stored in Patient Model Data Store 930 and used as additional training data to continue to develop and refine the predictive capability of RMT-RNN over time.

Patient-specific data can be fed into the model to generate a patient-specific model, which can be stored in Patient Model Data Store 930. For example, imaging taken during a patient's initial visit may be fed into the general model to output diagnosis results. At a follow-up visit (e.g., six months) for the same patient, the clinician will feed the patient's newly collected data from the follow-up visit into the online module. The online module will first find a matching cohort in training at the same follow up time interval, and then use the corresponding training model 507 to produce an updated diagnostic and prognostic result for the patient 508. In another aspect, longitudinal imaging taken across multiple visits may be used to generate a patient-specific model for more accurate diagnosis and prognosis results or to project changes in impairment over time. An extended IMTL-DL could be applied to longitudinal data to predict changes over time as impacted by variables including medications, dietary changes, exercise regimens, etc. In this aspect, the model could be used to identify variables or combinations of variables which result in maximal values for a specific patient. This output could be used to increase the effectiveness of clinical intervention in cognitive decline and aid in the reduction of progressive impairment between visits.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Referring now to FIG. 14, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 14 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

In some aspects, systems may be implemented on a standalone computing system. Referring now to FIG. 15, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 14). Examples of storage devices 26 include flash memory, magnetic hard drive, CD-ROM, and/or the like.

In some aspects, systems may be implemented on a distributed computing network, such as one having any number of clients and/or servers. Referring now to FIG. 16, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 15. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

FIG. 17 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for diagnostics and prognostics of mild cognitive impairment, comprising:
   a computer system comprising a memory and a processor;
   a deep learning engine, comprising a first plurality of programming instructions stored in the memory and operating on the processor, wherein the first plurality of programming instructions, when operating on the processor, causes the computer system to:
     retrieve a plurality of patient data;
     process the data into training data subsets;
     use the one or more training data subsets to train one or more predictive diagnosis and prognosis-related deep learning models, wherein each of the one or more predictive diagnosis and prognosis-related deep learning models are trained using a different training data subset;
     apply transfer learning to the one or more predictive diagnosis and prognosis-related deep learning models to integrate available modalities, wherein the integrated modalities are used to train a deep learning classifier to output an accurate diagnostic or prognostic prediction;
     receive a diagnosis or prognosis-related request for a target patient;
     retrieve a plurality of target patient data;
     input the target patient data into the deep learning classifier; and
     output the target patient's prediction
   wherein the deep learning engine is further configured to:
     train a predictive model of a target patient;
     find one or more matches between the deep learning classifier and the predictive model of the target patient;
     use the one or more matches to identify diagnosis or prognosis-related predictions of the target patient; and
     output the target patient's predictions.

2. The system of claim 1, wherein the plurality of patient data comprises medical imaging data, medical non-imaging data, and a combination of both.

3. The system of claim 1, further comprising an image processing engine, comprising a second plurality of programming instructions stored in the memory and operating on the processor, wherein the second plurality of programming instructions, when operating on the processor, causes the computer system to:
   receive medical imaging data;
   preprocess the medical imaging data; and
   send the preprocessed medical imaging data to the deep learning engine.

4. The system of claim 1, further comprising a data processing pipeline, comprising a third plurality of programming instructions stored in the memory and operating on the processor, wherein the third plurality of programming instructions, when operating on the processor, causes the computer system to:
  receive medical non-imaging data;
  preprocess the medical non-imaging data; and
  send the preprocessed medical non-imaging data to the deep learning engine.

5. The system of claim 1, wherein the one or more deep learning models is a reverse multi-task recurrent neural network and wherein the deep learning classifier is a reverse multi-task recurrent neural network.

6. The system of claim 1, wherein the target patient's predictive model is updated when new medical data becomes available.

7. The system of claim 6, wherein the updated target patient's predictive model outputs an updated diagnosis, prognosis, or both.

8. The system of claim 1, wherein the plurality of the target patient's medical data is incomplete.

9. The system of claim 1, wherein medical imaging data is selected from the group of MRI, FDG-PET, amyloid-PET, FLAIR, DTI, fMRI, Florbetapir-PET, and any combination thereof.

10. A method for diagnostics and prognostics of mild cognitive impairment, comprising the steps of:
  retrieving a plurality of patient data;
  processing the data into training data subsets;
  using the one or more training data subsets to train one or more predictive diagnosis and prognosis-related deep learning models, wherein each of the one or more predictive diagnosis and prognosis-related deep learning models are trained using a different training data subset;
  applying transfer learning to the one or more predictive diagnosis and prognosis-related deep learning models to integrate available modalities, wherein the integrated modalities are used to train a deep learning classifier to output an accurate diagnostic or prognostic prediction;
  receiving a diagnosis or prognosis-related request for a target patient;
  retrieving a plurality of target patient data;
  inputting the target patient data into the deep learning classifier;
  outputting the target patient's prediction;
  training a predictive model of a target patient;
  finding one or more matches between the deep learning classifier and the predictive model of the target patient;
  using the one or more matches to identify diagnosis or prognosis-related predictions of the target patient; and
  outputting the target patient's predictions.

11. The method of claim 10, wherein the plurality of patient data comprises medical imaging data, medical non-imaging data, and a combination of both.

12. The method of claim 10, further comprising the steps of:
  receiving medical imaging data;
  preprocessing the medical imaging data; and
  sending the preprocessed medical imaging data to the deep learning engine.

13. The method of claim 10, further comprising the steps of:
  receiving medical non-imaging data;
  preprocessing the medical non-imaging data; and
  sending the preprocessed medical imaging data to the deep learning engine.

14. The method of claim 10, wherein the one or more deep learning models is a reverse multi-task recurrent neural network and wherein the deep learning classifier is a reverse multi-task recurrent neural network.

15. The method of claim 10, wherein the target patient's predictive model is updated when new medical data becomes available.

16. The method of claim 15, wherein the updated target patient's predictive model outputs an updated diagnosis, prognosis, or both.

17. The method of claim 10, wherein the plurality of the target patient's medical data is incomplete.

18. The method of claim 10, wherein medical imaging data is selected from the group of MRI, FDG-PET, amyloid-PET, FLAIR, DTI, fMRI, Florbetapir-PET, and any combination thereof.

* * * * *